US012805792B2

(12) United States Patent
Kim et al.

(10) Patent No.: US 12,805,792 B2
(45) Date of Patent: Nov. 24, 2026

(54) ELECTRONIC DEVICE FOR PROVIDING USER INTERFACE RELATED TO SLEEP STATE AND OPERATING METHOD THEREOF

(71) Applicant: Samsung Electronics Co., Ltd., Suwon-si (KR)

(72) Inventors: Hyogil Kim, Suwon-si (KR); Yonghak Lee, Suwon-si (KR); Donghyun Lee, Suwon-si (KR); Jeongyup Han, Suwon-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 711 days.

(21) Appl. No.: 18/320,505

(22) Filed: May 19, 2023

(65) Prior Publication Data

US 2023/0293096 A1 Sep. 21, 2023

Related U.S. Application Data

(63) Continuation of application No. PCT/KR2022/008586, filed on Jun. 17, 2022.

(30) Foreign Application Priority Data

Jul. 14, 2021 (KR) ........................ 10-2021-0092381

(51) Int. Cl.
*A61B 5/00* (2006.01)
*A61B 5/369* (2021.01)
(Continued)

(52) U.S. Cl.
CPC .......... *A61B 5/4812* (2013.01); *A61B 5/7264* (2013.01); *A61B 5/7275* (2013.01);
(Continued)

(58) Field of Classification Search
CPC ... A61B 5/4812; A61B 5/7264; A61B 5/7275; A61B 5/7282; A61B 5/6898;
(Continued)

(56) References Cited

U.S. PATENT DOCUMENTS 9,173,811 B2 11/2015 Greiner et al.
10,307,331 B2 6/2019 Greiner et al.
(Continued)

FOREIGN PATENT DOCUMENTS

CN 107205659 A 9/2017
CN 112716449 A 4/2021
(Continued)

OTHER PUBLICATIONS

Translation KR 20140039452 A (Year: 2014).*
(Continued)

*Primary Examiner* — Carrie R Dorna
*Assistant Examiner* — Joshua Daryl D Lannu
(74) *Attorney, Agent, or Firm* — Jefferson IP Law, LLP

(57) ABSTRACT

An electronic device for providing a user interface related to a sleep state and an operating method thereof are provided. The electronic device includes a communication circuit, a memory, and at least one processor. The least one processor may be configured to acquire real-time sleep data of a user with regard to a unit sleep session, detect an abnormal rapid eye movement (REM) sleep event based on the real-time sleep data and the user's previous sleep data with regard to a full sleep session, and provide a user interface based on designated action information in response to the abnormal REM sleep event.

20 Claims, 12 Drawing Sheets

(51) Int. Cl.

| | |
|---|---|
| ***A61B 5/398*** | (2021.01) |
| ***A61M 21/00*** | (2006.01) |
| ***A61M 21/02*** | (2006.01) |
| ***G16H 20/70*** | (2018.01) |

(52) U.S. Cl.
CPC ........... *A61B 5/7282* (2013.01); *A61M 21/02* (2013.01); *A61M 2021/0083* (2013.01)

(58) Field of Classification Search
CPC ......... A61B 5/746; A61B 5/369; A61B 5/398; A61B 5/4809; A61B 5/4815; A61B 5/486; A61M 21/02; A61M 2021/0083; A61M 2021/0022; A61M 2021/0027; A61M 2205/3561; A61M 2021/005; A61M 2205/18; A61M 2205/3592; A61M 2205/505; A61M 2205/52; A61M 2209/088; A61M 2210/0612; A61M 2210/083; A61M 2230/04; A61M 2230/63; A61M 2021/0044; G16H 20/70
See application file for complete search history.

(56) References Cited

U.S. PATENT DOCUMENTS

| | | | | |
|---|---|---|---|---|
| 10,534,900 | B2 | 1/2020 | Cheong et al. | |
| 2008/0234785 | A1 * | 9/2008 | Nakayama ........... | A61B 5/4035 607/62 |
| 2009/0198145 | A1 * | 8/2009 | Chow .................. | A61K 31/661 600/595 |
| 2015/0245800 | A1 | 9/2015 | Sorensen et al. | |
| 2020/0237295 | A1 | 7/2020 | Lee et al. | |
| 2021/0178112 | A1 | 6/2021 | Ning et al. | |

FOREIGN PATENT DOCUMENTS

| | | | | | |
|---|---|---|---|---|---|
| JP | 2008-229248 | A | | 10/2008 | |
| JP | 2014-004091 | A | | 1/2014 | |
| JP | 2016028662 | A | | 3/2016 | |
| JP | 2016-131556 | A | | 7/2016 | |
| JP | 2017-086477 | A | | 5/2017 | |
| JP | 6536617 | A | | 7/2019 | |
| KR | 10-2012-0108488 | A | | 10/2012 | |
| KR | 10-2014-0039452 | A | | 4/2014 | |
| KR | 20140039452 | A | * | 4/2014 | ........... A61B 5/4806 |
| KR | 10-2015-0099430 | A | | 8/2015 | |
| KR | 20150099430 | A | * | 8/2015 | ............. G16H 10/00 |
| KR | 10-2017-0083483 | A | | 7/2017 | |
| KR | 10-1962812 | B1 | | 3/2019 | |
| KR | 10-2020-0033522 | A | | 3/2020 | |
| KR | 10-2250606 | B1 | | 5/2021 | |
| WO | 2019/162310 | A1 | | 8/2019 | |

OTHER PUBLICATIONS

Translation KR 20150099430 A (Year: 2015).*

European Search Report dated Sep. 16, 2024, issued in European Application No. 22842305.9.

Orthodox sleep, https://www.sleepnet.or.kr/sleep/normal Last retrieved May 19, 2023.

Maria Popova, Dreaming, Depression, and How Sleep Affects Emotions—The Atlantic https://www.theatlantic.com/health/archive/2012/08/dreaming-depression-and-how-sleep-affects-emotions/261051 Aug. 13, 2012.

Palagini, et al., REM sleep dysregulation in depression: state of the art https://pubmed.ncbi.nlm.nih.gov/23391633/ Feb. 5, 2013.

Cano-Lozano, et al., A review of sleep disorders in depression https://pubmed.ncbi.nlm.nih.gov/12599137/ Feb. 2003.

Dr. Michael Breus, Depression and Sleep https://thesleepdoctor.com/mental-health/depression-and-sleep/ Dec. 13, 2022.

Riemann, et al., Sleep, insomnia, and depression https://www.nature.com/articles/s41386-019-0411-y May 9, 2019.

Hale, FDA clears Apple Watch sleep app that intervenes to stop nightmares caused by PTSD https://www.fiercebiotech.com/medtech/fda-clears-apple-watch-sleep-app-intervenes-to-stop-nightmares-caused-by-ptsd Nov. 10, 2020.

International Search Report dated Oct. 5, 2022, issued in an International No. PCT/KR2022/008586.

Korean Office Action with English translation dated Apr. 23, 2026; Korean Appln. No. 10-2021-0092381.

Indian Office Action dated Aug. 11, 2026; Indian Appln. No. 202417005130.

Chinese Office Action with English translation dated Aug. 21, 2026; Chinese Appln. No. 202280037063.7.

* cited by examiner

ELECTRONIC DEVICE FOR PROVIDING USER INTERFACE RELATED TO SLEEP STATE AND OPERATING METHOD THEREOF

CROSS-REFERENCE TO RELATED APPLICATION(S)

This application is a continuation application, claiming priority under § 365(c), of an International application No. PCT/KR2022/008586, filed on Jun. 17, 2022, which is based on and claims the benefit of a Korean patent application number 10-2021-0092381, filed on Jul. 14, 2021, in the Korean Intellectual Property Office, the disclosure of which is incorporated by reference herein in its entirety.

TECHNICAL FIELD

The disclosure relates to an electronic device configured to provide a user interface according to a sleep state, and a method for operating the same. More particularly, the disclosure relates to an electronic device and a method for operating the same, wherein a sleep state related to rapid eye movement (REM) sleep among a user's sleep activities can be monitored in real time, or a user interface can be provided as a feedback according to the result of monitoring.

BACKGROUND ART

In line with development of mobile communication technologies, electronic devices having portability or mobility (for example, smartphones, wearable devices) have been widely used, and more diversified functions are provided through electronic devices. For example, an electronic device may be used to continuously monitor the user's biometric data and to manage health (health care service).

An electronic device (for example, a smartphone) may acquire the user's biometric data from another electronic device (for example, a wearable device) capable of interworking with one or more sensors or with the electronic device, and may analyze the user's health state based on the acquired biometric data. The electronic device may monitor the exercise state while the user is active or may monitor the sleep state while the user sleeps and may provide feedbacks according to the result of monitoring such that the user can maintain healthy physical and metal conditions.

The above information is presented as background information only to assist with an understanding of the disclosure. No determination has been made, and no assertion is made, as to whether any of the above might be applicable as prior art with regard to the disclosure.

DISCLOSURE

Technical Problem

In line with increasing interests in health, functions regarding sleep activities closely related to health have been proposed. Currently, an electronic device (for example, a smartphone) may analyze the user's sleep based on biometric data collected through interworking with one or more sensors provided in the electronic device or with another electronic device (for example, a wearable device), and may provide the user with the result of analysis.

Sleep may be classified into rapid eye movement (REM) sleep and non-REM sleep.

REM sleep is a stage of sleep characterized by rapid eye movements, which is shallow sleep close to an awake state. The criterion of REM sleep may include not only rapid eye movements, but also a low degree of muscle tone and a low voltage of electroencephalography (EEG). Such characteristics are commonly found in a polysomnogram test for diagnosing sleep disorders.

An adult's REM sleep may generally correspond to about 20-25% (for example, about 90-120 minutes) of the total sleep. When sleeping at night, a person commonly experiences five stages of REM sleep (REM cycle). Many animals and some people tend to wake up or sleep very shallowly for a short period of time after a phase of REM sleep has passed.

Sleep activities may be closely related to the user's health or mental/physical condition. An electronic device may be used to monitor REM sleep among sleep stages and to provide feedbacks according to the result, thereby contributing to the user's health or condition improvement by supporting healthy sleep activities.

More particularly, in connection with depression, insomnia or excessive sleep is utilized as a major diagnosis criterion (DSM-IV) of depression, and research results implying that intentionally preventing REM sleep could help cure depression have been provided. In reality, a depression cure may act in such a manner that a correct sleep cycle is supported by influencing REM sleep.

However, existing electronic devices require the full sleep cycle to identify REM sleep, and this poses a limitation in that real-time monitoring of REM sleep or instant feedback is difficult.

Aspects of the disclosure are to address at least the above-mentioned problems and/or disadvantages and to provide at least the advantages described below. Accordingly, an aspect of the disclosure is to provide an electronic device and a method for operating the same, wherein a sleep state related to REM sleep among the user's sleep activities can be monitored in real time, or a user interface can be provided as a feedback according to the result of monitoring.

Another aspect of the disclosure is to provide an electronic device and a method for operating the same, wherein a criterion for determining REM sleep can be applied while being customized to the individual user.

Another aspect of the disclosure is to provide an electronic device and a method for operating the same, wherein the user is controlled so as not to remain in abnormal REM sleep, thereby helping treat depression.

Additional aspects will be set forth in part in the description which follows and, in part, will be apparent from the description, or may be learned by practice of the presented embodiments.

Technical Solution

In accordance with an aspect of the disclosure, an electronic device is provided. The electronic device includes a communication circuit, a memory, and at least one processor operatively connected to the communication circuit and the memory. The memory stores instructions which, when executed, cause the at least one processor to acquire real-time sleep data of a user with regard to a unit sleep session, detect an abnormal rapid eye movement (REM) sleep event based on the real-time sleep data and the user's previous sleep data with regard to a full sleep session, and provide a user interface based on designated action information in response to the abnormal REM sleep event.

In accordance with another aspect of the disclosure, a method for operating an electronic device is provided. The method includes acquiring real-time sleep data of a user with regard to a unit sleep session, detecting an abnormal rapid eye movement (REM) sleep event based on the real-time sleep data and the user's previous sleep data with regard to a full sleep session, and providing a user interface based on designated action information in response to the abnormal REM sleep event.

Advantageous Effects

According to various embodiments of the disclosure, a sleep state related to REM sleep among the user's sleep activities is monitored in real time, or a user interface is provided as a feedback according to the result of monitoring.

According to various embodiments of the disclosure, a REM sleep determination criterion customized to each user is applied, thereby enabling accurate REM sleep determination.

According to various embodiments of the disclosure, the user is controlled so as not to remain in abnormal REM sleep, thereby helping treat depression.

Other aspects, advantages, and salient features of the disclosure will become apparent to those skilled in the art from the following detailed description, which, taken in conjunction with the annexed drawings, discloses various embodiments of the disclosure.

DESCRIPTION OF DRAWINGS

The above and other aspects, features, and advantages of certain embodiments of the disclosure will be more apparent from the following description taken in conjunction with the accompanying drawings, in which.

Throughout the drawings, it should be noted that like reference numbers are used to depict the same or similar elements, features, and structures.

MODE FOR INVENTION

The following description with reference to the accompanying drawings is provided to assist in a comprehensive understanding of various embodiments of the disclosure as defined by the claims and their equivalents. It includes various specific details to assist in that understanding but these are to be regarded as merely exemplary. Accordingly, those of ordinary skill in the art will recognize that various changes and modifications of the various embodiments described herein can be made without departing from the scope and spirit of the disclosure. In addition, descriptions of well-known functions and constructions may be omitted for clarity and conciseness.

The terms and words used in the following description and claims are not limited to the bibliographical meanings, but, are merely used by the inventor to enable a clear and consistent understanding of the disclosure. Accordingly, it should be apparent to those skilled in the art that the following description of various embodiments of the disclosure is provided for illustration purpose only and not for the purpose of limiting the disclosure as defined by the appended claims and their equivalents.

It is to be understood that the singular forms "a," "an," and "the" include plural referents unless the context clearly dictates otherwise. Thus, for example, reference to "a component surface" includes reference to one or more of such surfaces.

Figure 1:
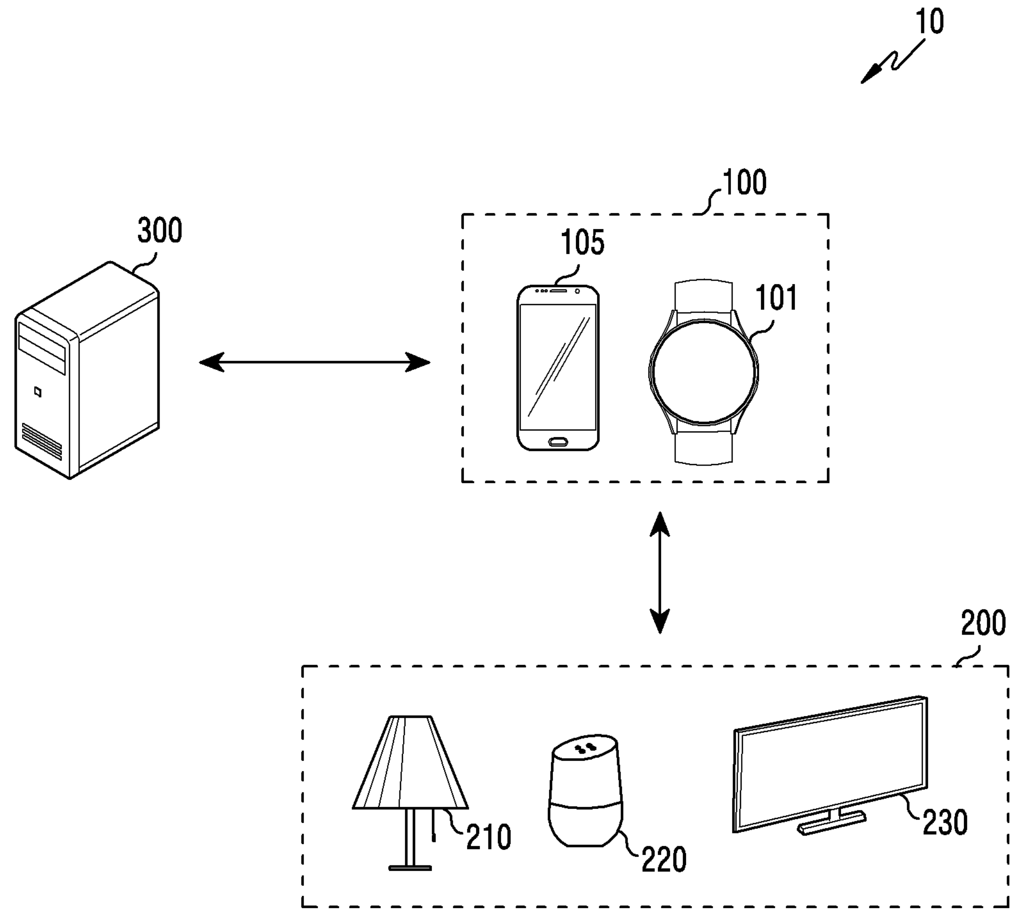
FIG. 1 illustrates a system including an electronic device according to an embodiment of the disclosure.

FIG. 1 illustrates a system including an electronic device according to an embodiment of the disclosure.

Referring to FIG. 1, the system may include a wearable device 101, a mobile device 105, one or more Internet of things (IoT) devices 200 (e.g., a smart lamp 210, a smart speaker 220, and a smart television (TV) 230), and/or an external server 300.

In an embodiment of the disclosure, the wearable device 101 may be a wearable-type device. The wearable device 101 may be a device having a weight or battery capacity that a user may use without any difficulty in daily life or while sleeping. For example, the wearable device 101 may be one of a smart watch, a smart band, a smart ring, and smart socks.

In an embodiment of the disclosure, at least a part of the wearable device 101, the mobile device 105, and the one or more IoT devices 200 may be operatively and/or functionally (or operatively) connected via short-range wireless communication (e.g., Bluetooth™, Bluetooth low energy (BLE), near field communication (NFC), or wireless fidelity (Wi-Fi)) so as to enable interworking with each other.

In an embodiment of the disclosure, the wearable device 101 (e.g., a smart watch) may perform a biometric signal measurement function. The wearable device 101 may be in a state worn by the user during sleep.

For example, the wearable device 101 may include at least one sensor (e.g., an electrode, an electrocardiography (ECG) sensor, or a photoplethysmogram (PPG) sensor) for measuring a biometric signal and a motion sensor (e.g., an acceleration sensor and a gyro sensor). The wearable device 101 may measure, through the at least one sensor, a biometric signal (e.g., a cardiac activity signal) of a user wearing the wearable device 101 and/or a motion signal according to the user's movement.

In an embodiment of the disclosure, the wearable device 101 may perform a sleep monitoring function.

For example, the wearable device 101 may calculate inter-beat interval (IBI) data from the user's cardiac activity signal (e.g., an electrocardiogram signal and a pulse signal), and may monitor whether a REM sleep stage is occurring and/or whether an abnormal REM sleep event is occurring, by using the calculated inter-beat interval (IBI) data.

In an embodiment of the disclosure, the wearable device 101 may perform a sleep control function based on a sleep monitoring result. The sleep control function may be a function of providing a user interface to induce a user to wake up or induce the user to fall into deep sleep.

For example, when an abnormal REM sleep event occurs as a result of sleep monitoring, the wearable device 101 may identify designated action information and provide a user interface according to the action information. The action information may be information designating one or more actions (e.g., alarm output, vibration output, lighting control, and audio reproduction) relating to an abnormal REM sleep event. The action information may be preconfigured by the user. For example, the user may execute an application (e.g., a health care application and a sleep care application) in the wearable device 101 or the mobile device 105, and may configure through an app execution screen one or more actions to be performed when an abnormal REM sleep event occurs. The corresponding action information may be stored in one of the wearable device 101, the mobile device 105, and the external server 300.

The wearable device 101 may provide a user interface according to designated action information.

The user interface may be provided through at least a part of the wearable device 101, the mobile device 105, and the one or more IoT devices 200. For example, the wearable device 101 may be connected to the IoT device 200 through short-range wireless communication to interwork with the corresponding IoT device 200, and may provide a user interface through the corresponding IoT device 200. As another example, the wearable device 101 or the mobile device 105 may provide a user interface by itself. As another example, the wearable device 101 may notify the mobile device 105 of the occurrence of an abnormal REM sleep event, or may transmit designated action information to the mobile device 105. In this case, the mobile device 105 may provide a user interface by itself and/or through one or more IoT devices 200.

The user interface may be implemented by a visual type (e.g., lamp turn-on, lamp brightness, and screen), an audible type (e.g., audio such as music and sound), a tactile type (e.g., vibration), or a hybrid type obtained by combining at least a part thereof. For example, the smart lamp 210 may be turned on or the brightness level of the smart lamp 210 which has been already turned on may increase. As another example, a designated audio (e.g., sleep-inducing music, a user's favorite song, a sound of a designated pattern) may be output through the smart speaker 220. As another example, vibration may be output from the wearable device 101 or the mobile device 105. As another example, the display of the wearable device 101 or the mobile device 105 is turned on, and a message notifying of the occurrence of an abnormal REM sleep event or information regarding the abnormal REM sleep event (e.g., real-time sleep chart) may be displayed on the screen of the display.

The wearable device 101 may transmit the user's sleep data to the mobile device 105 through short-range wireless communication. The sleep data may correspond to the user's biometric signal measured during sleep. When a REM sleep event occurs and/or when an abnormal REM sleep event occurs, the wearable device 101 may transmit the corresponding event information to the mobile device 105 together with the sleep data.

The mobile device 105 may be connected to the wearable device 101 and/or one or more IoT devices 200 through short-range wireless communication. The mobile device 105 may receive sleep data transmitted from the wearable device 101. The mobile device 105 may provide a user interface by itself according to designated action information, or may control one or more IoT devices 200 so as to provide a user interface through the IoT devices 200.

The wearable device 101 and/or the mobile device 105 may be communicatively connected to the external server 300. For example, the external server 300 may be a remote server connected through long-distance wireless communication (e.g., cellular communication, $5^{th}$ generation (5G) communication, and Internet). As another example, the external server 300 may be a home server connected through short-range wireless communication (e.g., Bluetooth™, BLE, NFC, and Wi-Fi).

The external server 300 may receive and record at least a part of the user's sleep data, event information regarding a REM sleep event, or event information regarding an abnormal REM sleep event from the wearable device 101 or the mobile device 105.

For convenience, in FIG. 1, the system has been described by assuming that the electronic device 100 according to an embodiment corresponds to the wearable device 101 (e.g., a smart watch), the wearable device 101 performs a biometric signal measurement function and a sleep monitoring function, and the mobile the device 105 performs a sleep control function for providing a user interface in conjunction with the wearable device 101. However, the disclosure is not limited thereto. For example, the electronic device 100 according to an embodiment may correspond to the mobile device 105 (e.g., a smart phone). In this case, the electronic device 100 may operate in conjunction with the wearable device 101 for performing a biometric signal measurement function. As another example, the electronic device 100 may perform functions of the wearable device 101 and/or the mobile device 105 in a selective or combination manner. Alternatively, the electronic device 100 may integrally perform the function of the wearable device 101 and the function of the mobile device 105.

Figure 2:
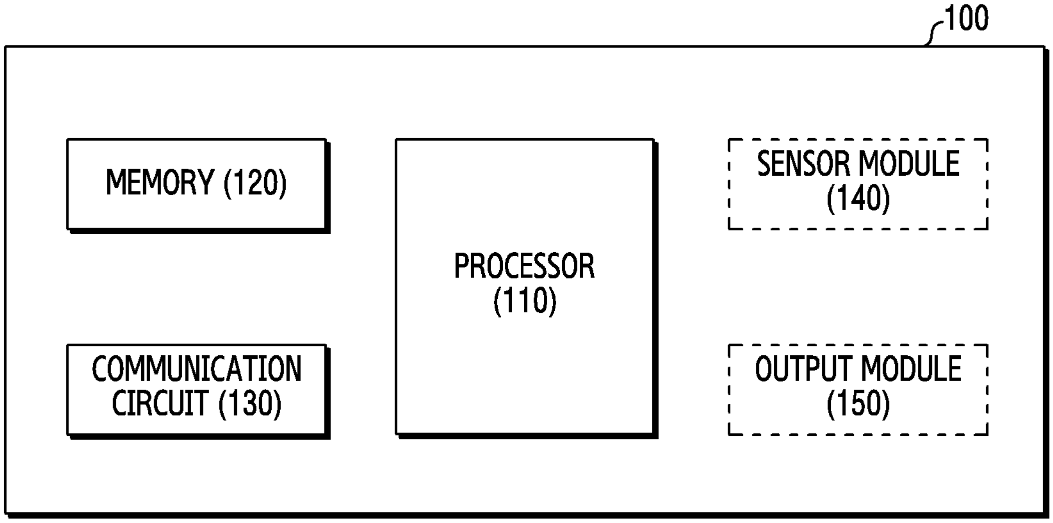
FIG. 2 is a block diagram of an electronic device according to an embodiment of the disclosure.

FIG. 2 is a block diagram of an electronic device according to an embodiment of the disclosure.

For example, the electronic device 100 according to an embodiment may correspond to the wearable device 101 and/or the mobile device 105 of FIG. 1. The electronic device 100 may correspond to an electronic device 1001 of FIG. 10 to be described later, or may include at least some of the elements of the electronic device 1001.

Referring to FIG. 2, the electronic device 100 (e.g., the wearable device 101) according to an embodiment may include a processor 110, a memory 120, and/or a communication circuit 130. The electronic device 100 may further include a sensor module 140 or an output module 150. The electronic device 100 may omit at least one of the elements or may additionally include other elements.

At least a part of the processor 110, the memory 120, the communication circuit 130, the sensor module 140, and/or the output module 150 included in the electronic device 100 may be electrically and/or operatively connected to each other, so as to exchange signals (such as commands or data) with each other.

Figure 10:
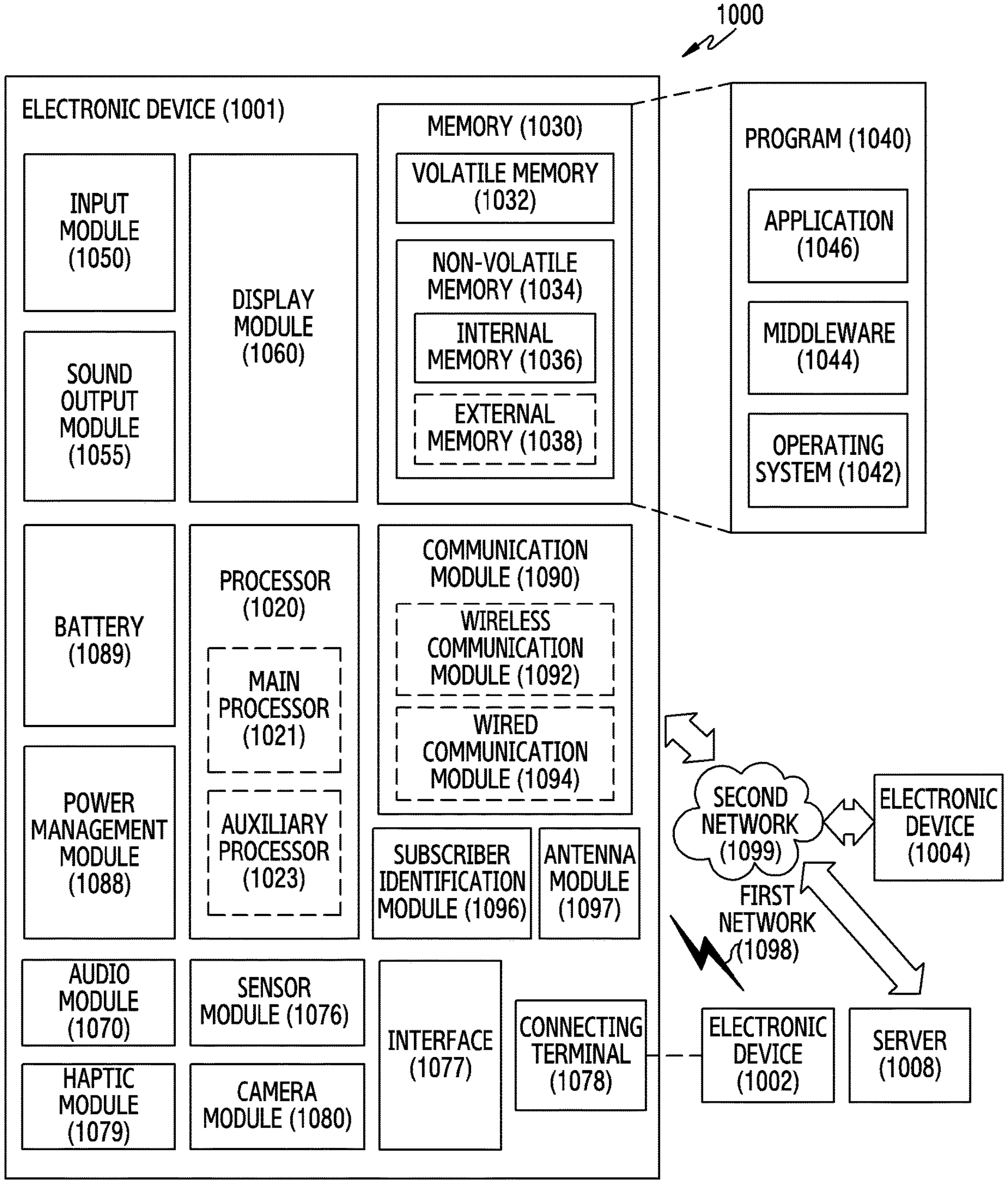
FIG. 10 is a block diagram of an electronic device in a network environment according to an embodiment of the disclosure.

The electronic device 100 may include at least a part of the electronic device 1001 illustrated in FIG. 10. For example, the processor 110 may correspond to a processor 1020 (one of processors 1021 and 1023) of FIG. 10. The memory 120 may include at least a part of a memory 1030 of FIG. 10. The communication circuit 130 may include a communication module 1090 of FIG. 10. The sensor module 140 may correspond to or include a part of a sensor module 1076 of FIG. 10. The output module 150 may include at least a part of a display module 1060, an audio module 1070, a sound output module 1055, and a haptic module 1079 of FIG. 10.

The processor 110 may execute and/or control various functions supported by the electronic device 100. The processor 110 may control at least a part of the memory 120, the communication circuit 130, the sensor module 140, and the output module 150. The processor 110 may execute an application by executing a code written in a programming language stored in the memory 120 of the electronic device 100, and may control various hardware. For example, the processor 110 may execute an application (e.g., a sleep care application, a health care application, and a fitness application) to provide at least one of a biometric signal measurement function, a sleep monitoring function, and a sleep control function by using the application. An application executed in the electronic device 100 may operate independently or in conjunction with an external electronic device (e.g., the mobile device 105 or the external server 300 of FIG. 1).

According to execution of the instructions stored in the memory 120, an operation of the processor 110 may be performed.

In an embodiment of the disclosure, the sensor module 140 may include at least one sensor. The sensor module 140 may include a first sensor (e.g., an electrode, an ECG sensor, and a PPG sensor) and/or a second sensor (e.g., an acceleration sensor and a gyro sensor). The first sensor may measure a user's biometric signal (e.g., a cardiac activity signal, such as an electrocardiogram signal or a pulse signal). The second sensor may include an acceleration sensor, a gyro sensor, or a combination thereof (e.g., a 6-axis sensor). However, the disclosure is not limited thereto, and the second sensor may include all sensors capable of measuring a motion signal according to the user's movement (e.g., tossing and turning or moving) (or the movement of the electronic device 100 worn by the user).

In an embodiment of the disclosure, the communication circuit 130 may correspond to a wireless communication module (e.g., a wireless communication module 1092 of FIG. 10). The communication circuit 130 may establish a communication connection with one or more external electronic devices (e.g., the mobile device 105 or the external server 300 of FIG. 1), and may perform transmission/reception of various data. For example, the communication circuit 130 may support at least one communication method of Bluetooth™, BLE, NFC, Wi-Fi for short-range wireless communication, or cellular communication, 5G communication, and Internet for long-distance wireless communication.

In an embodiment of the disclosure, the processor 110 may perform at least one of a biometric signal measurement function, a sleep monitoring function, and a sleep control function.

In an embodiment of the disclosure, the processor 110 may acquire real-time sleep data of the user for a unit sleep session (e.g., 5 minutes). The real-time sleep data may include data regarding one or more of a biometric signal measured through a first sensor (e.g., an electrode, an ECG sensor, and a PPG sensor) in the sensor module 140, a biometric signal received from an external electronic device (e.g., the wearable device 101 or the mobile device 105 of FIG. 1) through the communication circuit 130, a motion signal measured through a second sensor (e.g., an acceleration sensor and a gyro sensor) in the sensor module 140, or a motion signal received from an external electronic device (e.g., the wearable device 101 or the mobile device 105 of FIG. 1) through the communication circuit 130.

In an embodiment of the disclosure, the processor 110 may detect an abnormal rapid eye movement (REM) sleep event based on the user's real-time sleep data relating to a unit sleep session and the user's previous sleep data relating to a full sleep session. The unit sleep session may be a short-term sleep session. The full sleep session may be a long-term sleep session.

The abnormal REM sleep event may be detected based on at least one of a time of entering a first REM sleep stage, a frequency of occurrence of a REM sleep stage, a duration of a REM sleep stage, and an interval between REM sleep stages.

The previous sleep data may correspond to data relating to the user's past sleep activity repeated a designated number of times (e.g., 7 times) or more for a designated time period (e.g., 7 hours), or the user's past sleep data for a recent predetermined period (e.g., 7 days).

In an embodiment of the disclosure, the processor 110 may identify personalized boundary information for detecting the REM sleep stage of the user from the user's previous sleep data relating to a full sleep session (e.g., 7 hours). The personalized boundary information may be feature information of a cardiac activity signal (e.g., an electrocardiogram signal or a pulse signal) measured during the full sleep session. The feature information may include one or more an LF value (power in low frequency range), an HF value (power in high frequency range), and an LF/HF value (ratio of LF to HF).

The processor 110 may determine whether the pattern of the REM sleep stage is an abnormal pattern based on the user's real-time sleep data and the personalized boundary information. The processor 110 may detect an abnormal REM sleep event based on that the pattern of the REM sleep stage is the abnormal pattern.

In an embodiment of the disclosure, the processor 110 may calculate inter-beat interval (IBI) data from a cardiac activity signal, such as an electrocardiogram signal or a pulse signal, and may detect an REM sleep stage and/or abnormal REM sleep event by using the detected inter-beat interval (IBI) data.

In an embodiment of the disclosure, the processor 110 may provide a user interface based on designated action information in response to the abnormal REM sleep event. The action information may include information regarding at least one action of alarm output, vibration output, lighting control, and audio reproduction. The action information may include information on an action for inducing a user to wake up or inducing the user to fall into deep sleep.

For example, the processor 110 may provide a user interface related to the action information through the output module 150. As another example, the processor 110 may perform short-range wireless communication with at least one external electronic device (e.g., the mobile device 105 or one or more IoT devices 200 of FIG. 1) through the communication circuit 130 so as to provide the user interface related to the action information through the at least one external electronic device.

In an embodiment of the disclosure, the processor 110 may acquire real-time sleep data relating to a full sleep session by accumulating real-time sleep data relating to multiple unit sleep sessions. The processor 110 may transmit at least one of real-time sleep data relating to the full sleep session, information on an abnormal REM sleep event, and action execution information related to an abnormal REM sleep event to the external server 300 through the communication circuit 130, so as to back up the data and information.

Figure 3:
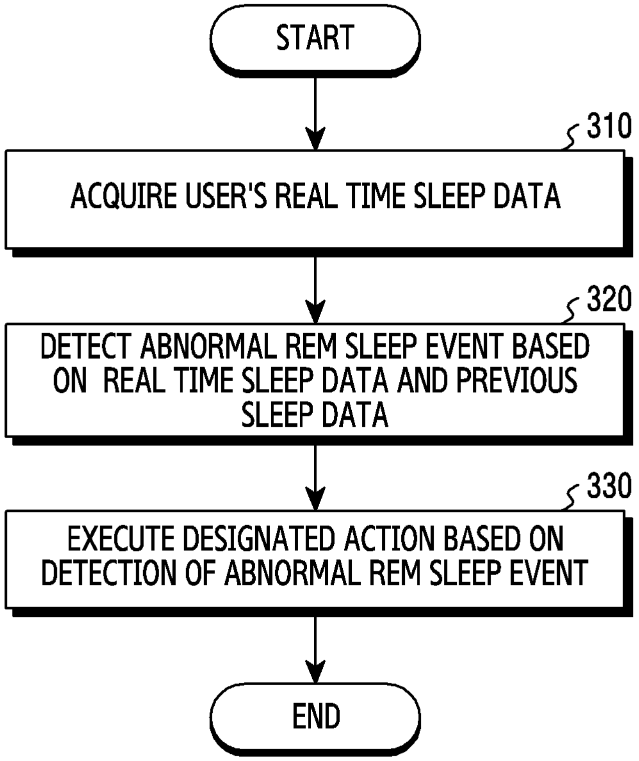
FIG. 3 is a flowchart illustrating a method for operating an electronic device according to an embodiment of the disclosure.

FIG. 3 is a flowchart illustrating a method for operating an electronic device according to an embodiment of the disclosure.

For convenience, a method of FIG. 3 is assumed to be performed by the electronic device 100 (e.g., the wearable device 101) of FIG. 2, but is not limited thereto. For example, the method of FIG. 3 may be performed by an electronic device (e.g., the processor 110 of FIG. 2, an application (e.g., a sleep care application) executed in the electronic device 100 of FIG. 2, and an electronic device 1001 or a processor 1020 of FIG. 10). In some embodiments of the disclosure, at least one of the operations of the method illustrated in FIG. 3 may be omitted, the order of some operations may be changed, or other operations may be added.

Referring to FIG. 3, the electronic device 100 (e.g., the wearable device 101 of FIG. 1) may be in a state worn by a user during sleep activity. The electronic device 100 (e.g., the wearable device 101) may be connected to at least one external electronic device 100 (e.g., the mobile device 105 and the IoT device 200) through short-range wireless communication so as to enable interworking with each other.

In operation 310, the electronic device 100 may acquire the user's real-time sleep data relating to a unit sleep session (e.g., 5 minutes) for the analysis of the user's sleep.

In an embodiment of the disclosure, the real-time sleep data may be data corresponding to a detection signal (e.g., a biometric signal and/or a motion signal) or data identified (or detected or processed) from the detection signal. For example, the detection signal may include a biometric signal obtained through a first sensor (e.g., a biosensor, such as an electrode, an ECG sensor, or a PPG sensor), and/or a motion signal obtained through a second sensor (e.g., an acceleration sensor or a gyro sensor).

In an embodiment of the disclosure, the real-time sleep data may include data regarding one or more of a biometric signal measured through a first sensor (e.g., a biosensor, such as an electrode, an ECG sensor, and a PPG sensor) in the electronic device 100, a biometric signal received from the external electronic device 100 through the communication circuit 130, a motion signal measured through a second sensor (e.g., an acceleration sensor or a gyro sensor) in the electronic device 100, or a motion signal received from the external electronic device 100 through the communication circuit 130. For example, the acquisition of real-time sleep data may be repeatedly performed continuously or periodically.

In operation 320, an electronic device 1001 may detect an abnormal REM sleep event based on the real-time sleep data acquired through operation 310 and the user's previous sleep data relating to a full sleep session (e.g., 6 hours to 8 hours).

The previous sleep data may correspond to data relating to the user's past sleep activity repeated a designated number of times (e.g., 7 times) or more, or the user's past sleep data for a recent predetermined period (e.g., 7 days).

The abnormal REM sleep event may be detected based on at least one of a time of entering a first REM sleep stage, a frequency of occurrence of a REM sleep stage, a duration of a REM sleep stage, and an interval between REM sleep stages.

In operation 320, the electronic device 100 may identify personalized boundary information for detecting the REM sleep stage of the user from the user's previous sleep data. The personalized boundary information may be feature information of a cardiac activity signal measured during the full sleep session. The feature information may include one or more an LF value (power in low frequency range (e.g., 0.04-0.15 Hz)), an HF value (power in high frequency range (e.g., 0.15-0.4 Hz)), and an LF/HF value (ratio of LF to HF).

The electronic device 100 may determine whether the pattern of the REM sleep stage is an abnormal pattern based on the user's real-time sleep data and the personalized boundary information.

The electronic device 100 may detect an abnormal REM sleep event based on that the pattern of the REM sleep stage is an abnormal pattern.

In operation 330, the electronic device 100 may execute a designated action in response to the abnormal REM sleep event. The electronic device 100 may provide a user interface according to the designated action information. The action information may include information regarding at least one action of alarm output, vibration output, lighting control, and audio reproduction. The user interface according to the action information may be implemented as a visual type (e.g., lamp turn-on, lamp brightness, and screen), an audible type (e.g., audio, such as music and sound), a tactile type (e.g., vibration), or a hybrid type obtained by combining at least a part thereof. The action information may include information on an action for inducing a user to wake up or inducing the user to fall into deep sleep. The action information may be preconfigured by a user.

In operation 330, the electronic device 100 may provide a user interface related to the designated action information through the output module 150 in the electronic device 100. Alternatively, the electronic device 100 may perform short-range wireless communication with at least one external electronic device 100 (e.g., the mobile device 105 or IoT device 200) through the communication circuit 130 in the electronic device 100, so as to provide the user interface related to the designated action information through the at least one external electronic device 100.

For example, the user may execute an application (e.g., a sleep care application) in the electronic device 100 (e.g., the wearable device 101 or the mobile device 105), and may configure one or more actions, which are to be performed at the time of detecting the abnormal REM sleep event, through the corresponding application execution screen, so as to store action information regarding the at least one action.

The action information may be information for performing an action through at least a part of the wearable device 101, the mobile device 105, and the one or more IoT devices 200 when the abnormal REM sleep event is detected. The action may be an action for inducing a user to wake up or an action for inducing the user to fall into deep sleep.

An action to be performed upon detection of the abnormal REM sleep event may be designated by reflecting a user's preference. For example, the user may configure an action to play the music he or she prefers or listens to frequently.

The output level of the user interface to be provided at the time of detecting the abnormal REM sleep event may be controlled to an appropriate level. For example, when causing a person to wake up or sleep in offline, strong stimuli (e.g., sound equal to or greater than a predetermined volume, lamp brightness equal to or greater than a predetermined level, sudden lamp turn-on, or strong level of vibration) may surprise a person and may not be suitable for sleep control or treatment of depression.

Accordingly, an action to be performed or a user interface to be provided in response to the abnormal REM sleep event may be controlled at an appropriate level (e.g., a level weaker than the normal level).

As an example, the electronic device 100 may perform control such that a vibration of a weak level among multiple levels (e.g., a weak level, a normal level, a strong level) is to be output through the wearable device 101 (e.g., a smart watch). As another example, the electronic device 100 may turn on the IoT device 200 (e.g., the smart lamp 210) with low illumination. As another example, the electronic device 100 may induce the user to get out of REM sleep for a while by reproducing soft music through the IoT device 200 (e.g., the smart speaker 220). As another example, the electronic device 100 may induce the user to fully wake up by turning on the smart TV 230.

A user interface to be provided upon detection of an abnormal REM sleep event may be provided differently depending on whether the user sleeps alone. For example, the electronic device 100 may interwork with the IoT device 200 (e.g., a smart device (not shown) attachable to a bed or a smart device (not shown) that provides a function to scan the user's surroundings), so as to determine whether the user sleeps alone or with someone other than the user. When it is determined that the user is sleeping alone, the electronic device 100 may provide a user interface of a visual type (e.g., lamp turn-on, lamp brightness, and screen) and/or a user interface of an auditory type (e.g., audio, such as music and sound). When the electronic device 100 determines that the user is sleeping with someone other than the user, the wearable device 101 worn by the user may provide a tactile type (e.g., vibration) user interface.

In an embodiment of the disclosure, the electronic device 100 may acquire real-time sleep data relating to a full sleep session by accumulating real-time sleep data relating to multiple unit sleep sessions. In addition, the electronic device 100 may transmit one or more of real-time sleep data relating to the full sleep session, event information regarding the abnormal REM sleep event, and execution information relating to functions to the external server 300, so as to back up the data and information through the external server 300.

The electronic device 100 may detect, even if full sleep is not completed, the occurrence of the REM sleep stage in real time from real-time sleep data collected during sleep (e.g., real-time sleep data for 5 minutes) by using personalized boundary information extracted from previous sleep data during a full sleep session covering the full sleep.

Figure 9A:
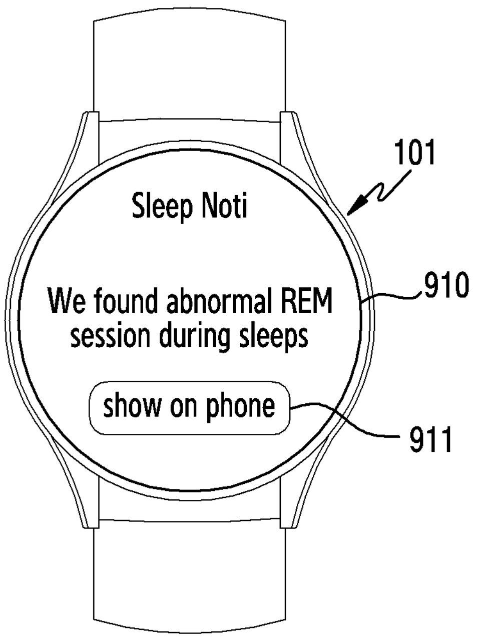
FIG. 9A illustrates a user interface displayed on an electronic device according to an embodiment of the disclosure.
Figure 9B:
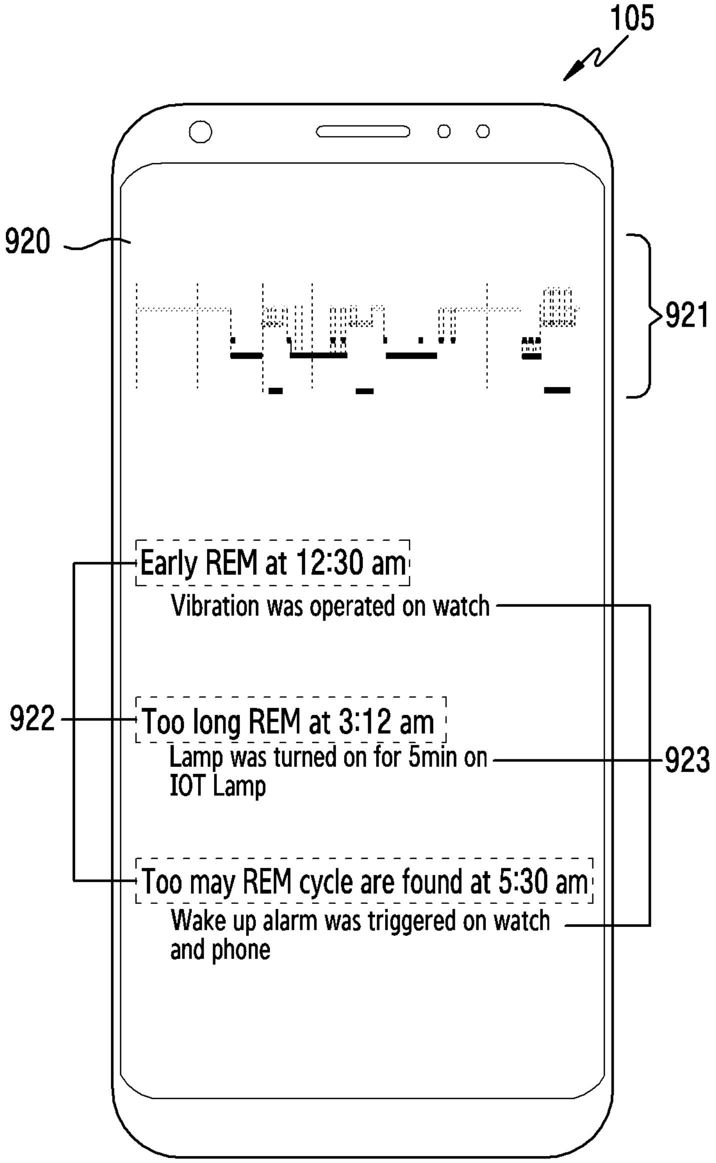
FIG. 9B illustrates a user interface displayed on an electronic device according to an embodiment of the disclosure.
Figure 9C:
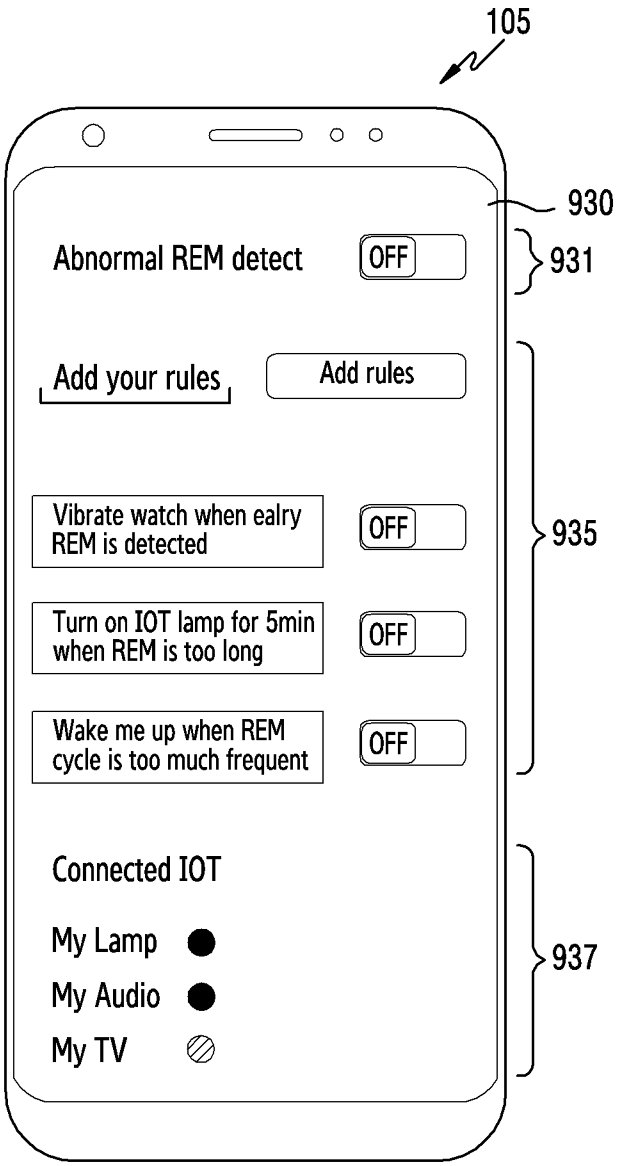
FIG. 9C illustrates a user interface displayed on an electronic device according to an embodiment of the disclosure.

FIGS. 9A, 9B, and 9C, which will be described later, illustrate user interfaces that may be provided in various embodiments of the disclosure.

The method for operating the electronic device according to various embodiments may further include operating an application in at least one external electronic device (e.g., the mobile device 105 or IoT device 200) or the electronic device 100, and configuring through an app execution screen one or more actions to be performed when the abnormal REM sleep event occurs. The application may include at least one of a health care application or a sleep care application.

Figure 4:
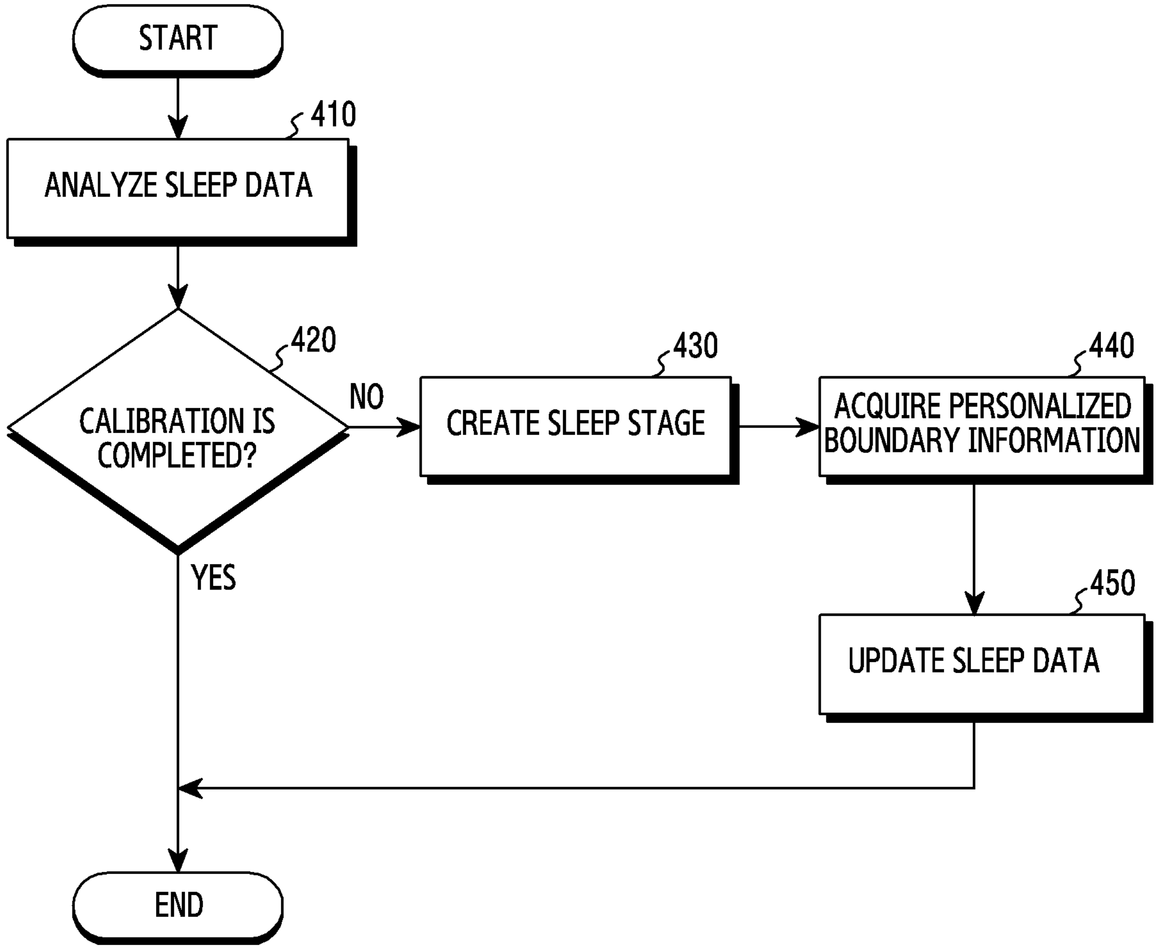
FIG. 4 is a flowchart illustrating an operation of identifying personalized boundary information according to an embodiment of the disclosure.

FIG. 4 is a flowchart illustrating an operation of identifying personalized boundary information according to an embodiment of the disclosure.

For example, the operation of FIG. 4 may correspond to a part of the operation 320 of FIG. 3. For example, through the operation of FIG. 4, personalized boundary information required for determining whether a user is in a REM sleep stage may be identified. In operation 320 of FIG. 3, the REM sleep stage of the user may be detected based on the personalized boundary information.

Referring to FIG. 4, in operation 410, the electronic device 100 may collect and analyze the user's sleep data during the user's sleep activity. For example, the sleep data may include biometric data collected through one or more sensors (e.g., an electrode, an ECG sensor, a PPG sensor, an acceleration sensor, or a gyro sensor) provided in the electronic device 100, and/or biometric data collected in conjunction with the external electronic device 100.

In operation 420, the electronic device 100 may determine whether calibration has been completed. The calibration may include an operation of acquiring the user's personalized boundary information. For example, the electronic device 100 may determine whether the user's personalized boundary information exists (or whether the user's personalized boundary information is stored in the memory 120 or the external server 300). The electronic device 100 may identify the personalized boundary information based on the user's previous sleep data repeated a designated number of times (e.g., 7 times) or more during a full sleep session (e.g., 6 hours or more to 8 hours). The personalized boundary information may be feature information of a cardiac activity signal measured during a full sleep session. The feature information may include one or more an LF value (power in low frequency range (e.g., 0.04~0.15 Hz)), an HF value (power in high frequency range (e.g., 0.15~0.4 Hz)), and an LF/HF value (ratio of LF to HF).

As a result of the determination in operation 420, when the calibration is not completed, the process may proceed to operation 430.

In operation 430, the electronic device 100 may create sleep stages based on the user's sleep data relating to a full sleep session corresponding to full sleep.

Full sleep may be divided into non-REM sleep and REM sleep.

Figure 5:
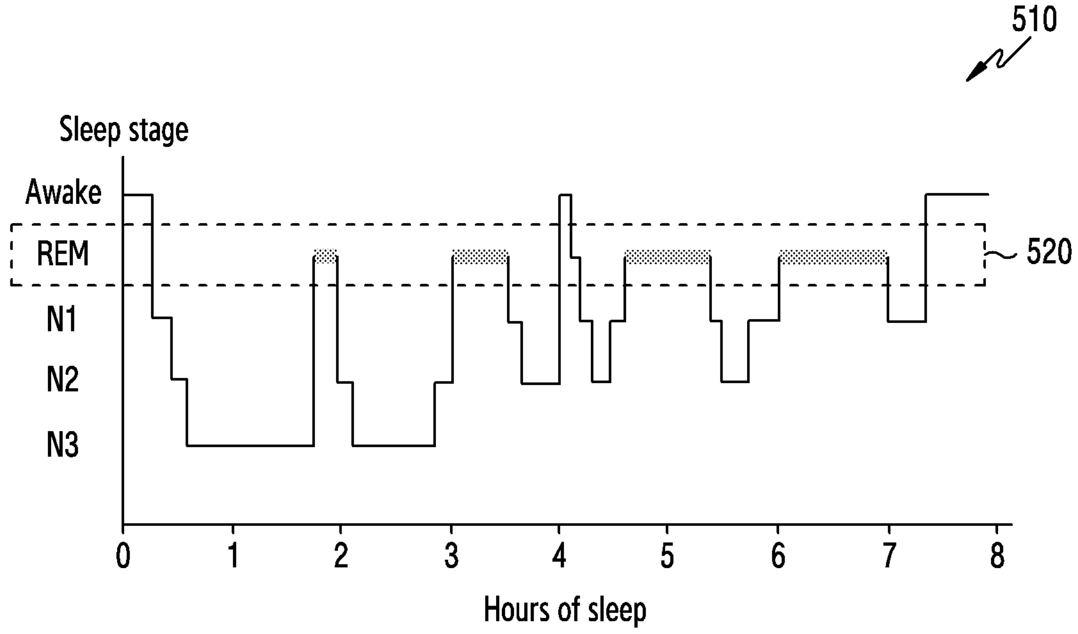
FIG. 5 is a graph illustrating sleep stages according to an embodiment of the disclosure.

FIG. 5 is a graph 510 illustrating sleep stages according to an embodiment of the disclosure.

Referring to FIG. 5, a full sleep session (e.g., 7 hours) may be classified into a non-REM sleep session corresponding to a non-REM sleep stage and a REM sleep session corresponding to a REM sleep stage 520. The non-REM sleep session may be divided into three sleep stages (N1 (wake), N2 (light), N3 (deep)) according to the depth. N1 and N2 may be classified as light sleep, and N3 may be classified as deep sleep or slow wave sleep.

Since the activities of the sympathetic and parasympathetic nervous systems are different in the REM and non-REM sleep stages and the response of these nervous systems is expressed as a cardiac activity, cardiac activity signals (e.g., electrocardiogram signals or pulse signals) or heart rate variability (HRV) signals detected therefrom may be used to distinguish between the REM sleep stage and the non-REM sleep stage.

The graph of FIG. 5 may correspond to a normal sleep pattern. When it is not normal sleep, for example, in a case of sleep of a depressed patient, an abnormal pattern different from the normal sleep pattern by a predetermined degree or more may occur. For example, a time taken to enter the first REM sleep stage, a frequency of occurrence of the REM sleep stage, a duration of the REM sleep stage, and an interval between the REM sleep stages may be different from those of the normal sleep pattern.

According to an embodiment of the disclosure, the electronic device 100 may detect the pattern of the user's REM sleep stage by using the user's personalized boundary information, and may determine whether the pattern of the REM sleep stage indicates an abnormal pattern.

Referring back to FIG. 4, in operation 440, the electronic device 100 may obtain boundary information of the REM sleep stage created in operation 430. The obtained boundary information may be used as personalized boundary information for detecting the user's REM sleep stage.

In operation 450, the electronic device 100 may update the user's previous sleep data. For example, the previous sleep data is data personalized to the user, and may include at least a part of the user's sleep data relating to a full sleep session collected in operation 410, the information regarding sleep stages created in operation 430, and the personalized boundary information acquired through operation 440.

Figure 6:
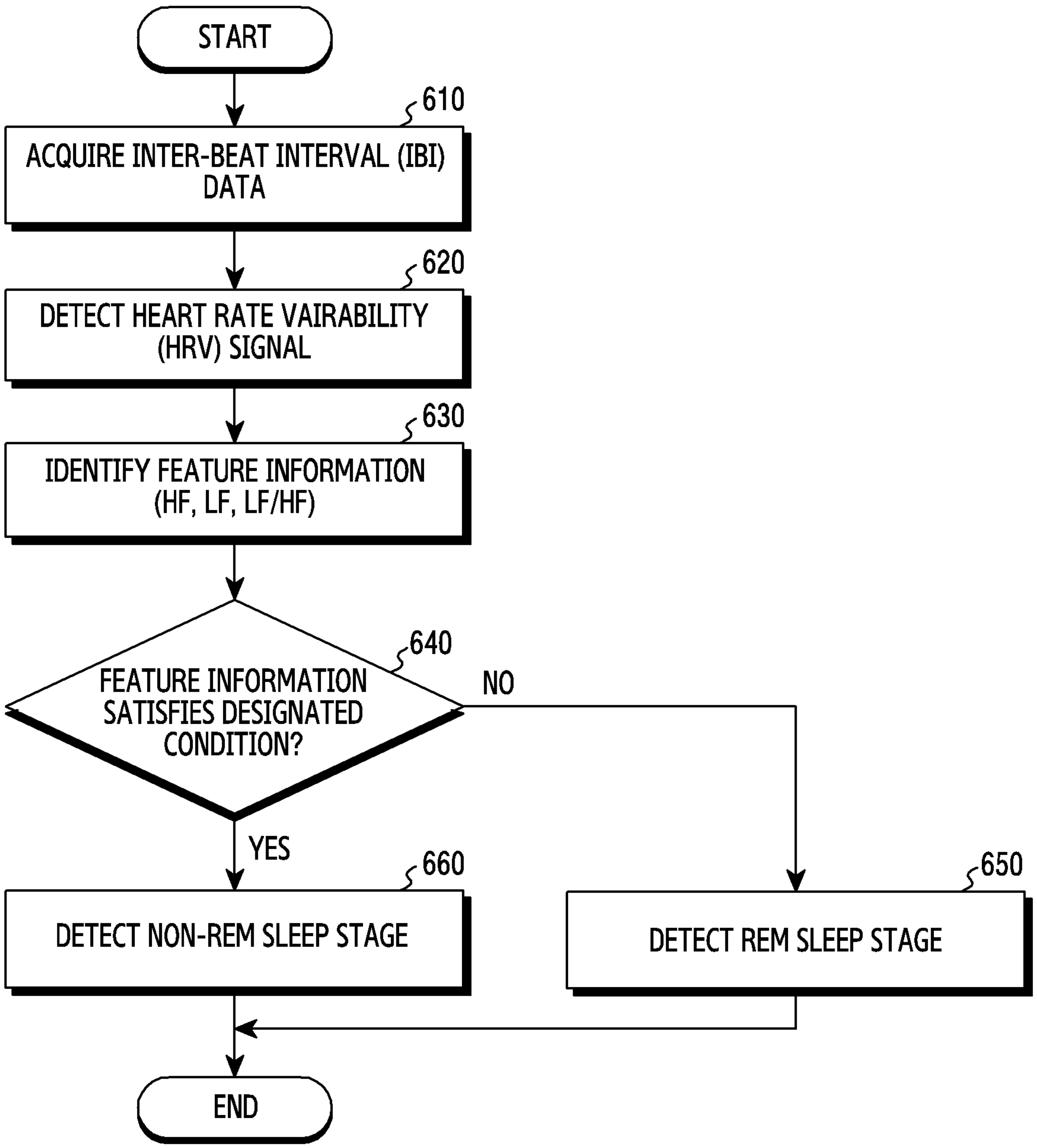
FIG. 6 is a flowchart illustrating an operation of detecting a REM sleep stage according to an embodiment of the disclosure.

FIG. 6 is a flowchart illustrating an operation of detecting a REM sleep stage according to an embodiment of the disclosure.

For example, the operation of FIG. 6 may correspond to a part of the operation 320 of FIG. 3. For example, operation 320 of FIG. 3 may include at least a part of the operations of FIG. 6 for detecting a REM sleep stage. For example, in operation 320, the electronic device 100 may detect one or more REM sleep stages through the operation of FIG. 6.

In an embodiment of FIG. 6, the electronic device 100 may detect a heart rate variability (HRV) signal from a user's cardiac activity signal (e.g., an electrocardiogram signal or a pulse signal) measured in real time, and may detect the REM sleep stage by performing sleep analysis based on the heart rate variability (HRV) signal.

Referring to FIG. 6, in operation 610, the electronic device 100 may acquire real-time sleep data. For example, the real-time sleep data may include data regarding a user's cardiac activity signal (e.g., an electrocardiogram signal or a pulse signal) measured in real time. The data regarding the cardiac activity signal may be data identified or detected from the cardiac activity signal or data obtained by processing the cardiac activity signal.

For example, data regarding the cardiac activity signal may correspond to inter-beat interval (IBI) (or RR interval (RRI)) data. The inter-beat interval (IBI) data may be data indicating an interval between heartbeats, and may indicate a time difference between adjacent peaks of the cardiac activity signal. The electronic device 100 may calculate the peaks of the cardiac activity signal by using a peak detection algorithm to obtain inter-beat interval (IBI) data.

For example, the electronic device 100 may calculate inter-beat interval (IBI) data by using at least one of an algorithm of finding the vertices of a cardiac activity signal (e.g., an electrocardiogram signal and/or a pulse signal) and calculating an interval therebetween (peak to peak detection algorithm); an algorithm of finding and calculating the starting point of a signal (valley to valley detection algorithm); or an algorithm of finding and calculating a part with the largest slope from the differential values of the signal (zero-crossing point detection algorithm).

In operation 620, the electronic device 100 may detect a heart rate variability (HRV) signal indicating a change in the inter-beat interval (IBI) by using the inter-beat interval (IBI) data obtained through operation 610.

For example, the electronic device 100 may detect a heart rate variability (HRV) signal from the cardiac activity signal by using a method of arranging the inter-beat interval (IBI) data obtained from the cardiac activity signal on a time axis and converting the IBI data into a time series signal.

Heart rate may be determined by the effect of the autonomic nervous system on the inherent spontaneity of pacemaker cells in a sinoatrial node. The sinoatrial node may be controlled by the sympathetic and parasympathetic nerves, and their conflicting effects are balanced to determine heart rate. The effect of the autonomic nervous system influencing the sinoatrial node may change every moment according to changes in the body and/or external environment, and this periodic change in heart rate according to a time may be referred to as heart rate variability (HRV). Heart rate variability (HRV) signals are related to interactions between sympathetic and parasympathetic nerves influencing the sinoatrial node, and may reflect spontaneous heart rate and RR interval (RRI) fluctuations.

In operation 630, the electronic device 100 may identify (or extract) feature information of a cardiac activity signal measured in real time using the heart rate variability (HRV) signal detected through operation 620. For example, the feature information may be information obtainable (or extractable) by converting a heart rate variability (HRV) signal in a time domain into a HRV signal in a frequency domain. For example, the feature information may include at least one of an HF value, an LF value, and an LF/HF value identified through power spectrum analysis of the heart rate variability (HRV) signal.

The electronic device 100 may identify (or extract) feature information by analyzing the heart rate variability (HRV) signal in a time domain and/or a frequency domain.

For example, the electronic device 100 may identify (extract) the standard deviation of the RR interval (SDNN) indicating a change in heartbeat, a root mean square of successive differences of RR interval (RMSSD) indicating a parasympathetic nerve activity of the heart, or mean of RR interval (mean RR) through a statistical method in the time domain.

For example, the electronic device 100 may identify (or extract), in the frequency domain, a total power in a very low frequency (VLF, <0.04 Hz), a low frequency (LF, 0.04~0.15 Hz), and a high frequency (HF, 0.15-0.4 Hz) band for a predetermined time (e.g., 5 minutes) indicating the overall degree of activity of the autonomic nervous system, an LF value indicating the degree of activity of the sympathetic nerve (power in low frequency range), an HF value indicating the degree of activity of the parasympathetic nerve (power in high frequency), a normalized LF value and HF value, and/or an LF/HF value indicating the overall balance of the autonomic nervous system (ratio of LF to HF).

In operation 640, the electronic device 100 may compare the feature information identified through operation 630 with the personalized boundary information to determine whether the two pieces of information correspond to each other. To this end, the electronic device 100 may identify the personalized boundary information for detecting the user's REM sleep stage from previous sleep data regarding the user's past full sleep. The personalized boundary information may be information included in previous sleep data and stored in advance, or information identified from the previous sleep data.

For example, a lower limit and an upper limit of the REM sleep stage may be designated by the personalized boundary information.

For example, the electronic device 100 may determine whether the HF value identified from the real-time sleep data satisfies a condition of being equal to or greater than a designated lower limit, and whether the LF/HF value determined from the real-time sleep data satisfies a condition of being equal to or smaller than a designated upper limit. For example, when the HF value identified from real-time sleep data corresponds to the lower limit designated by the personalized boundary information (e.g., within the error range (e.g., ±5%) of the HF value identified from previous sleep data), the HF value may be determined to satisfy a condition of being equal to or greater than the designated lower limit. When the LF/HF value identified from real-time sleep data corresponds to the upper limit designated by the personalized boundary information (e.g., within the error range (e.g., ±5%) of the LF/HF value identified from the previous sleep data), the LF/HF value may be determined to satisfy a condition of being equal to or smaller than the designated upper limit As a result of the determination in operation 640, when the designated conditions are not satisfied, the electronic device 100 may proceed to operation 650 to detect the current sleep stage as a REM sleep stage.

As a result of the determination in operation 640, when the designated conditions are satisfied, the electronic device 100 may proceed to operation 660 to detect the current sleep stage as a non-REM sleep stage.

Figure 7A:
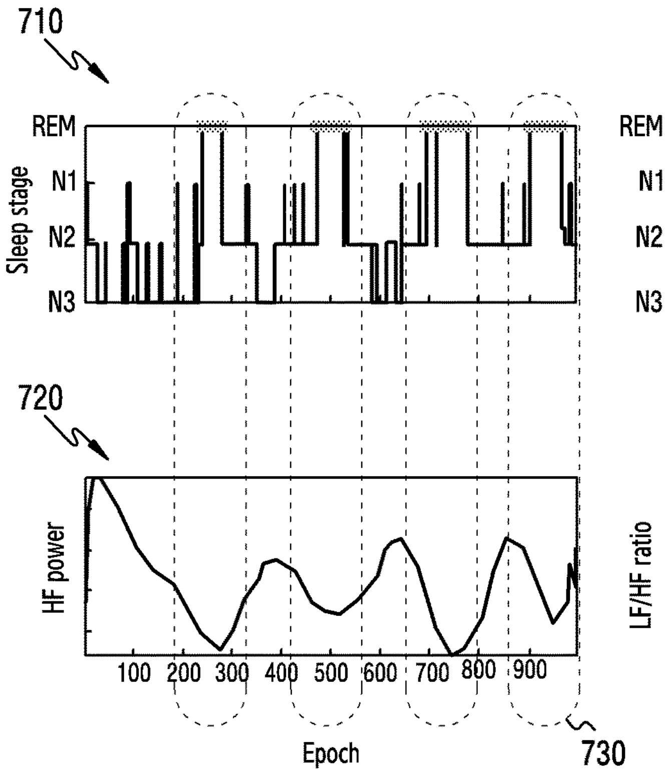
FIGS. 7A and 7B illustrate graphs for describing a correlation between feature information of biometric data and a REM sleep stage according to embodiments of the disclosure.
Figure 7B:
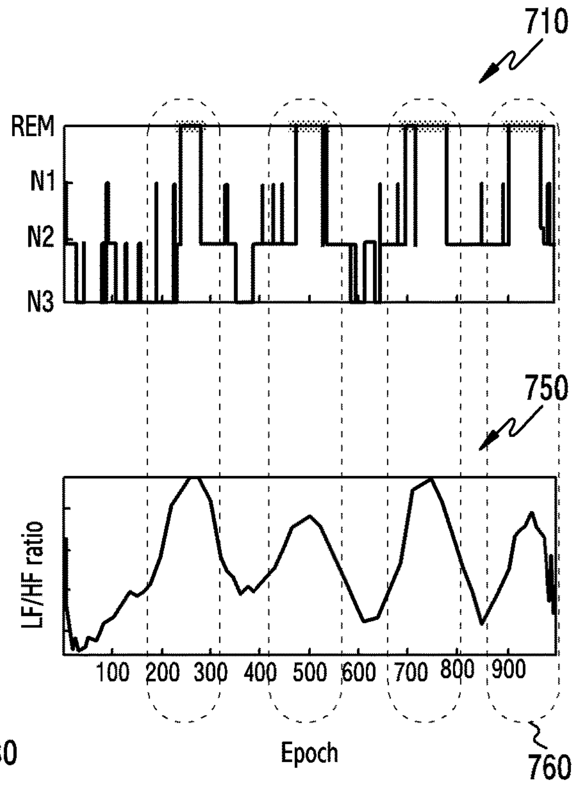

FIGS. 7A and 7B illustrate graphs for describing a correlation between feature information of a biometric signal and a REM sleep stage according to embodiments of the disclosure.

Referring to FIGS. 7A and 7B, the biometric signal is an electrocardiogram signal, and the feature information of the biometric signal may correspond to an LF/HF value (ratio of LF to HF) and an HF value of the electrocardiogram signal.

The electronic device 100 may use an LF/HF value (ratio of LF to HF) and an HF value of a backup electrocardiogram signal as personalized boundary information, and may estimate whether a user is in a REM sleep stage or in a non-REM sleep stage from the user's real-time electrocardiogram signal based on the personalized boundary information.

Referring to FIGS. 7A and 7B, reference numeral 710 is a graph illustrating sleep stages during full sleep. Reference numeral 720 is a graph illustrating a change of the HF value per unit time (epoch). Reference numeral 730 denotes REM sleep sessions and a range of HF values in each REM sleep session.

Reference numeral 750 is a graph showing a change in the LF/HF value (ratio of LF to HF) per unit time (epoch). Reference numeral 760 exemplifies REM sleep sessions and a range of LF/HF values (ratio of LF to HF) in each REM sleep session.

When the backup electrocardiogram signal of the user during full sleep is stored, the electronic device 100 may utilize the HF value and LF/HF value (ratio of LF to HF), which are feature information of the backup electrocardiogram signal, as personalized boundary information.

For example, a lower limit for detecting the user's REM sleep stage may be designated by the HF value. An upper limit for detecting the user's REM sleep stage may be designated by the LF/HF value.

For example, the electronic device 100 may determine whether the HF value of the real-time ECG signal satisfies a condition of being equal to or greater than the lower limit included in the personalized boundary information, and whether the LF/HF value (ratio of LF to HF) of the real-time ECG signal satisfies a condition of being equal to or smaller than an upper limit included in the personalized boundary information. For example, when the HF value of the real-time ECG signal corresponds to the lower limit designated by the personalized boundary information (e.g., within the error range (e.g., ±5%) of the average value of the HF values of the REM sleep sessions among the full sleep sessions of the backup ECG signal), the electronic device may determine that the HF value of the real-time ECG signal satisfies a condition of being equal to or greater than the designated lower limit FIG. 8 is a flowchart illustrating an operation of detecting an abnormal REM sleep event according to an embodiment of the disclosure.

Figure 8:
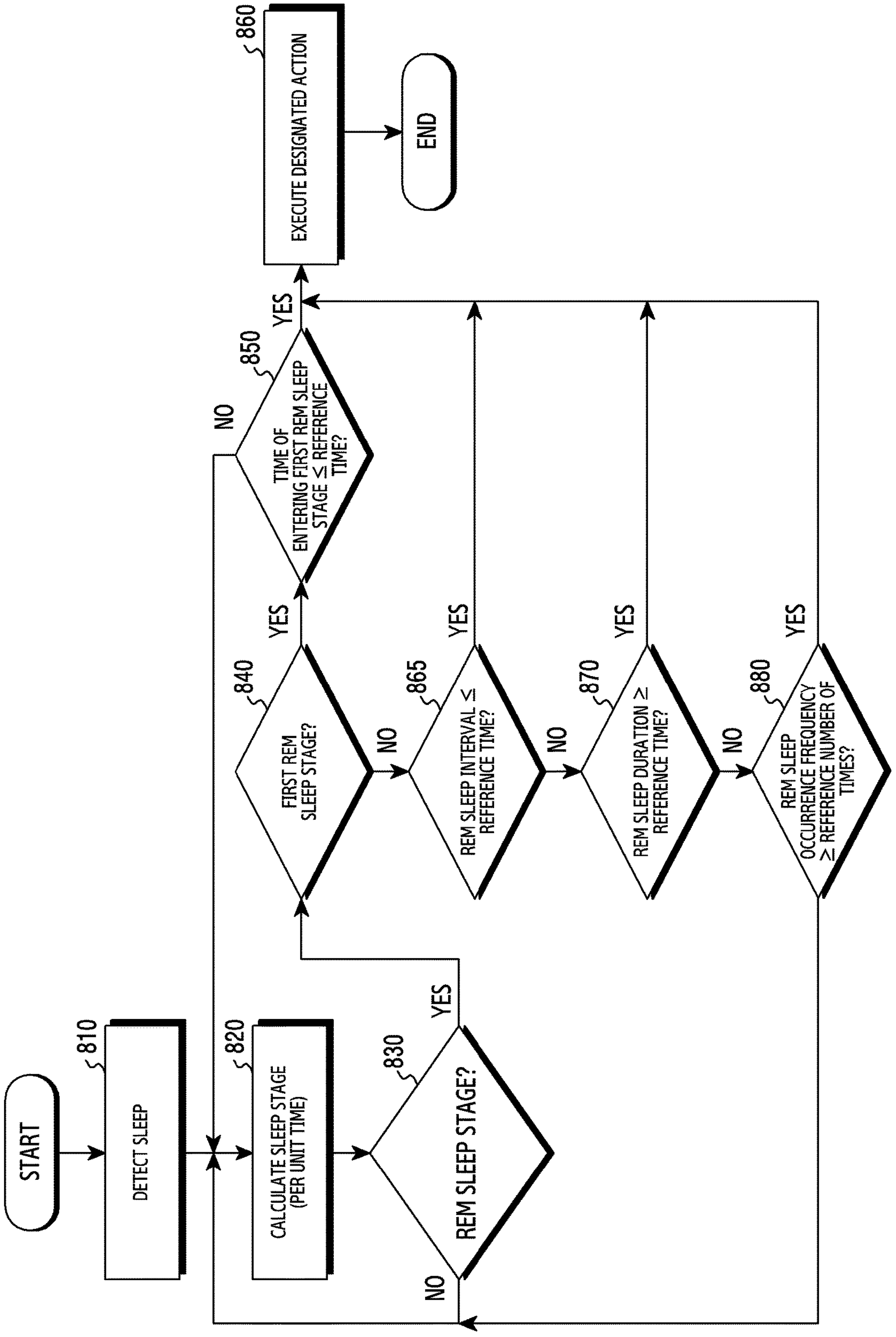
FIG. 8 is a flowchart illustrating an operation of detecting an abnormal REM sleep event according to an embodiment of the disclosure.

Referring to FIG. 8, the operation of FIG. 8 may correspond to a part of the operation 320 of FIG. 3. For example, operation 320 of FIG. 3 may include at least a part of the operations of FIG. 8 for detecting an abnormal REM sleep event. In some embodiments of the disclosure, at least one of the operations of a method illustrated in FIG. 8 may be omitted, the order of some operations may be changed, or other operations may be added.

The electronic device 100 may detect an abnormal REM sleep event based on at least one of a time of entering a first REM sleep stage, a frequency of occurrence of a REM sleep stage, a duration of the REM sleep stage, and an interval between REM sleep stages.

The electronic device 100 may detect a REM sleep stage and, when a time of detecting a first REM sleep stage is earlier than that of a normal pattern (e.g., 90 to 110 minutes after sleep initiation), may execute a designated action so that a user's REM sleep does not continue. In addition, the electronic device 100 may continuously observe the user's sleep activity and, when the interval between REM sleep stages is too short, the duration of the REM sleep stage is too long, or the frequency (or number) of REM sleep stages is too frequent, the electronic device may execute a designated action so as to control the user's abnormal REM sleep not to continue.

In operation 810, the electronic device 100 may detect a user's sleep activity or collect real-time sleep data. For example, the electronic device 100 may receive a motion signal of a user wearing the electronic device 100 and analyze the motion signal to detect sleep initiation. For example, the electronic device 100 may collect and monitor real-time sleep data while the user is sleeping.

When the user's sleep is initiated, raw data for sleep analysis may be collected through at least one sensor (e.g., an electrode, an ECG sensor, and a PPG sensor) for every unit sleep time (e.g., 5 minutes). The raw data may correspond to real-time sleep data. For example, the real-time sleep data may include at least a part of inter-beat interval (IBI) (or RRI) data obtained from the user's cardiac activity signal and/or data relating to a motion signal.

In operation 820, the electronic device 100 may periodically (e.g., every 5 minutes) calculate the user's current sleep stage by using the user's real-time sleep data. The electronic device 100 may identify the current sleep stage of the user by accumulating and analyzing real-time sleep data.

In operation 830, the electronic device 100 may determine whether the current sleep stage is a REM sleep stage based on the calculation result in operation 820.

As a result of the determination in operation 830, when the current sleep stage is the REM sleep stage, the electronic device 100 may proceed to operation 840 to determine whether the current REM sleep stage is a first REM sleep stage.

As a result of the determination in operation 840, when the current sleep stage is the first REM sleep stage, the electronic device 100 may proceed to operation 850 to determine whether a time of entering the first REM sleep stage (or the first REM sleep entering time) is too early. For example, the electronic device 100 may determine that a time of entering the first REM sleep stage is too early when a time taken from initiating the sleep to entering the first REM sleep stage is equal to or less than a reference time (e.g., 90 to 110 minutes).

As a result of the determination in operation 850, when a time of entering the first REM sleep stage is equal to or less than the reference time, the electronic device 100 may proceed to operation 860 to execute a designated action. In operation 860, the electronic device 100 may provide a user interface related to designated action information.

As a result of the determination in operation 840, when the current REM sleep stage is not the first REM sleep stage (e.g., in case of two or more REM sleep stages), the electronic device 100 may proceed to operation 865 to determine whether the interval between REM sleep stages (or REM sleep interval) is too short. For example, when a time between a previous REM sleep stage and a current REM sleep stage is equal to or less than a reference time (e.g., 60 minutes), the electronic device 100 may determine that the REM sleep session is too short.

As a result of the determination in operation 865, when the interval between REM sleep stages is equal to or less than the reference time, the electronic device 100 may proceed to operation 860 to execute a designated action.

As a result of the determination in operation 865, when the interval between REM sleep stages exceeds the reference time, the electronic device 100 may proceed to operation 870 to determine whether the duration of the current REM sleep stage (or REM sleep duration) is too long. For example, the electronic device 100 may count the duration of the current REM sleep stage and, when the corresponding time is equal to or greater than the reference time, the electronic device may determine that the duration of the current REM sleep stage is too long.

As a result of the determination in operation 870, when the duration of the current REM sleep stage is equal to or greater than the reference time, the electronic device 100 may proceed to operation 860 to execute a designated action.

As a result of the determination in operation 870, when the duration of the current REM sleep stage is less than the reference time, the electronic device 100 may proceed to operation 880 to determine whether the frequency of occurrence of the REM sleep stage (or the REM sleep occurrence frequency) is too frequent. For example, the electronic device 100 may determine that REM sleep occurs too frequently when the frequency of occurrence of the REM sleep stage is equal to or greater than the reference number of times (e.g., 4 to 5 times).

As a result of the determination in operation 880, when the frequency of occurrence of the REM sleep stage is equal to or greater than the reference number of times, the electronic device 100 may proceed to operation 860 to perform a designated action. In case that an abnormal REM sleep event occurs, for example, when a time of entering the first REM sleep stage is equal to or less than the reference time (e.g., 90 to 110 minutes after sleep initiation) as a result of the determination in operation 850, when the interval between REM sleep stages is equal to or less than the reference time (e.g., 60 minutes) as a result of the determination in operation 865, when the duration of the REM sleep stage is equal to or greater than the reference time as a result of the determination in operation 870, or when the frequency of occurrence of the REM sleep stage is equal to or greater than the reference number of times (e.g., 4 times) as a result of the determination in operation 880, the electronic device 100 may proceed to operation 860 to execute a designated action, thereby preventing the user's abnormal REM sleep from continuing.

In case that an abnormal REM sleep event does not occur, for example, when a time of entering the first REM sleep stage exceeds the reference time (e.g., 90 to 110 minutes after sleep initiation) as a result of the determination in operation 850, when the interval between REM sleep stages exceeds the reference time (e.g., 60 minutes) as a result of the determination in operation 865, when the duration of the REM sleep stage is less than the reference time as a result of the determination in operation 870, or when the frequency of occurrence of the REM sleep stage is less than the reference number of times (e.g., 4 times) as a result of the determination in operation 880, the electronic device 100 may return to operation 820 to calculate the user's current sleep stage periodically (e.g., every 5 minutes).

In an embodiment of the disclosure, the electronic device 100 may determine, for real-time feedback, whether an abnormal REM sleep event occurs by considering a unit sleep time or a current sleep time in which multiple unit sleep times are accumulated (a sleep time accumulated from a sleep start time to a current time).

For example, with reference to the full sleep session of normal sleep (e.g., 7 hours), if the reference number of times for the frequency of occurrence of REM sleep is 4 times, it may be appropriate to detect one REM sleep stage or less per one hour (reference number of times per unit time=1). When two or more REM sleep stages are detected (more than double the reference number of times per unit time) within one hour, it may be determined that an abnormal REM sleep event has occurred.

FIGS. 9A, 9B, and 9C below illustrate user interfaces that may be provided by the electronic device 100 (e.g., the wearable device 101 or the mobile device 105) according to various embodiments of the disclosure. For example, one or more screens among the screens shown in FIGS. 9A, 9B, and 9C may be displayed in the electronic device 100 according to various embodiments of the disclosure. For example, the screens may be an app execution screen displayed through an application (e.g., a sleep care application) running on the electronic device 100 (e.g., one of the wearable device 101 and the mobile device 105), or an application (e.g., a sleep care application) running in an external electronic device (e.g., the other one of the wearable device 101 and the mobile device 105) being connected with the electronic device 100 via short-distance wireless communication.

FIG. 9A illustrates a user interface displayed on an electronic device according to an embodiment of the disclosure.

Referring to FIG. 9A, a wearable device 101 may perform a sleep monitoring function, and may provide a user interface, such as a first screen 910 based on a result of the sleep monitoring. The first screen 910 may be a screen showing a sleep monitoring result of the wearable device 101.

As a result of the sleep monitoring, when an abnormal REM sleep event is detected, the wearable device 101 may display the first screen 910.

As shown, the first screen 910 may include a message indicating that an abnormal REM sleep event has occurred. A menu area 911 asking whether to view detailed sleep monitoring results through the mobile device 105 (e.g., a smart phone) may be displayed on the first screen 910.

The wearable device 101 and the mobile device 105 may be connected via short-range wireless communication. The wearable device 101 and the mobile device 105 may be logged in by the same user.

When the user wakes up and touches the menu area 911, the wearable device 101 may transmit a request to display the detailed sleep monitoring result to the mobile device 105.

FIG. 9B illustrates a user interface displayed on an electronic device according to an embodiment of the disclosure.

Referring to FIG. 9B, the mobile device 105 may receive a request to display the detailed sleep monitoring result from the wearable device 101.

The mobile device 105 may provide a user interface, such as a second screen 920 in response to the request. The second screen 920 may be a screen showing the detailed sleep monitoring result. The second screen 920 may be a screen showing an intermediate sleep monitoring result so far during sleep and an action executed according to a rule designated for each time zone.

As shown, the second screen 920 may include at least one of a first area 921 representing real-time sleep data (e.g., a real-time sleep chart) collected so far from the start of sleep, a second area 922 representing information regarding an abnormal REM sleep event, and a third area 923 representing action execution information related to the abnormal REM sleep event.

When an abnormal REM sleep event is detected, for example, as a result of sleep analysis, when the first REM sleep entering time is a designated time (e.g., 90 to 110 minutes after sleep initiation) or longer, when the interval between REM sleep stages is a designated time (e.g., 60 minutes) or less, when the duration of REM sleep is a designated time or longer, or when the frequency of occurrence of REM sleep is equal to or more than the designated number of times (e.g., 4-5 times based on 7 hours or 2 times or more in one hour), the mobile device 105 may display information on each event through the second area 922, and may display action execution information related to each event through the third area 923.

FIG. 9C illustrates a user interface displayed on an electronic device according to an embodiment of the disclosure.

Referring to FIG. 9C, the mobile device 105 may output a user interface, such as a third screen 930. The third screen 930 may be a screen for configuring one or more actions to be performed when an abnormal REM sleep event occurs.

A user may configure, through the third screen 930, rules for one or more actions to be performed when an abnormal REM sleep event occurs. The user may select, through the third screen 930, an action to be performed upon detection of an abnormal REM sleep event or an IoT device 200 for which the corresponding action is to be performed. The user may add, edit, or delete an action bound to a rule provided by an application (e.g., a sleep care application) through the third screen 930, thereby enabling sleep control according to a scenario desired by the user himself or herself.

As shown, the third screen 930 may include at least one of a first option area 931 for selecting whether to use the abnormal REM sleep detection function, a second option area 935 for configuring one or more rules to be performed when an abnormal REM sleep event is detected, and a third option area 937 for showing a device list for the IoT device 200 (e.g., the smart lamp 210, the smart speaker 220, and the smart TV 230) that may be used in conjunction with the abnormal REM sleep event.

For example, in the second option area 935, a first menu for turning on/off a vibration output function when the entry time to the first REM sleep stage is too early, a second menu for turning on/off a function of turning on the smart lamp 210 for a predetermined time period (e.g., 5 minutes) when the REM sleep stage is too long, and a third menu for turning on/off a function of performing an action (e.g., turn-on of the smart TV 230) of fully waking up the user when the REM sleep stage is too frequent may be displayed.

A display state of an icon corresponding to each device in the device list displayed in the third option area 937 may be changed according to a user input to the second option area 935. For example, when the user configures the first menu and the second menu as "on" and configures the third menu as "off" in the second option area 935, two icons indicating the smart lamp 210 and the smart speaker 220 in the third option area 937 may be displayed in a first color (e.g., green), and an icon indicating the smart TV 230 in the third option area 937 may be displayed in a second color (e.g., red) according to a user configuration.

FIG. 10 is a block diagram illustrating an electronic device in a network environment according to an embodiment of the disclosure.

Referring to FIG. 10, an electronic device 1001 in a network environment 1000 may communicate with an external electronic device 1002 via a first network 1098 (e.g., a short-range wireless communication network), or at least one of an external electronic device 1004 or a server 1008 via a second network 1099 (e.g., a long-range wireless communication network). According to an embodiment of the disclosure, the electronic device 1001 may communicate with the external electronic device 1004 via the server 1008. According to an embodiment of the disclosure, the electronic device 1001 may include a processor 1020, a memory 1030, an input module 1050, a sound output module 1055, a display module 1060, an audio module 1070, the sensor module 1076, an interface 1077, a connecting terminal 1078, a haptic module 1079, a camera module 1080, a power management module 1088, a battery 1089, a communication module 1090, a subscriber identification module (SIM) 1096, or an antenna module 1097. In some embodiments of the disclosure, at least one of the components (e.g., the connecting terminal 1078) may be omitted from the electronic device 1001, or one or more other components may be added in the electronic device 1001. In some embodiments of the disclosure, some of the components (e.g., the sensor module 1076, the camera module 1080, or the antenna module 1097) may be implemented as a single component (e.g., the display module 1060).

The processor 1020 may execute, for example, software (e.g., a program 1040) to control at least one other component (e.g., a hardware or software component) of the electronic device 1001 coupled with the processor 1020, and may perform various data processing or computation. According to one embodiment of the disclosure, as at least part of the data processing or computation, the processor 1020 may store a command or data received from another component (e.g., the sensor module 1076 or the communication module 1090) in a volatile memory 1032, process the command or the data stored in the volatile memory 1032, and store resulting data in a non-volatile memory 1034. According to an embodiment of the disclosure, the processor 1020 may include a main processor 1021 (e.g., a central processing unit (CPU) or an application processor (AP)), or an auxiliary processor 1023 (e.g., a graphics processing unit (GPU), a neural processing unit (NPU), an image signal processor (ISP), a sensor hub processor, or a communication processor (CP)) that is operable independently from, or in conjunction with, the main processor 1021. For example, when the electronic device 1001 includes the main processor 1021 and the auxiliary processor 1023, the auxiliary processor 1023 may be adapted to consume less power than the main processor 1021, or to be specific to a specified function. The auxiliary processor 1023 may be implemented as separate from, or as part of the main processor 1021.

The auxiliary processor 1023 may control at least some of functions or states related to at least one component (e.g., the display module 1060, the sensor module 1076, or the communication module 1090) among the components of the electronic device 1001, instead of the main processor 1021 while the main processor 1021 is in an inactive (e.g., a sleep) state, or together with the main processor 1021 while the main processor 1021 is in an active state (e.g., executing an application). According to an embodiment of the disclosure, the auxiliary processor 1023 (e.g., an image signal processor or a communication processor) may be implemented as part of another component (e.g., the camera module 1080 or the communication module 1090) functionally related to the auxiliary processor 1023. According to an embodiment of the disclosure, the auxiliary processor 1023 (e.g., the neural processing unit) may include a hardware structure specified for artificial intelligence model processing. An artificial intelligence model may be generated by machine learning. Such learning may be performed, e.g., by the electronic device 1001 where the artificial intelligence is performed or via a separate server (e.g., the server 1008). Learning algorithms may include, but are not limited to, e.g., supervised learning, unsupervised learning, semi-supervised learning, or reinforcement learning. The artificial intelligence model may include a plurality of artificial neural network layers. The artificial neural network may be a deep neural network (DNN), a convolutional neural network (CNN), a recurrent neural network (RNN), a restricted boltzmann machine (RBM), a deep belief network (DBN), a bidirectional recurrent deep neural network (BRDNN), deep Q-network or a combination of two or more thereof but is not limited thereto. The artificial intelligence model may, additionally or alternatively, include a software structure other than the hardware structure.

The memory 1030 may store various data used by at least one component (e.g., the processor 1020 or the sensor module 1076) of the electronic device 1001. The various data may include, for example, software (e.g., the program 1040) and input data or output data for a command related thereto. The memory 1030 may include the volatile memory 1032 or the non-volatile memory 1034.

The program 1040 may be stored in the memory 1030 as software, and may include, for example, an operating system (OS) 1042, middleware 1044, or an application 1046.

The input module 1050 may receive a command or data to be used by another component (e.g., the processor 1020) of the electronic device 1001, from the outside (e.g., a user) of the electronic device 1001. The input module 1050 may include, for example, a microphone, a mouse, a keyboard, a key (e.g., a button), or a digital pen (e.g., a stylus pen).

The sound output module 1055 may output sound signals to the outside of the electronic device 1001. The sound output module 1055 may include, for example, a speaker or a receiver. The speaker may be used for general purposes, such as playing multimedia or playing record. The receiver may be used for receiving incoming calls.

According to an embodiment of the disclosure, the receiver may be implemented as separate from, or as part of the speaker.

The display module 1060 may visually provide information to the outside (e.g., a user) of the electronic device 1001. The display module 1060 may include, for example, a display, a hologram device, or a projector and control circuitry to control a corresponding one of the display, hologram device, and projector. According to an embodiment of the disclosure, the display module 1060 may include a touch sensor adapted to detect a touch, or a pressure sensor adapted to measure the intensity of force incurred by the touch.

The audio module 1070 may convert a sound into an electrical signal and vice versa. According to an embodiment of the disclosure, the audio module 1070 may obtain the sound via the input module 1050, or output the sound via the sound output module 1055 or a headphone of an external electronic device (e.g., the external electronic device 1002) directly (e.g., wiredly) or wirelessly coupled with the electronic device 1001.

The sensor module 1076 may detect an operational state (e.g., power or temperature) of the electronic device 1001 or an environmental state (e.g., a state of a user) external to the electronic device 1001, and then generate an electrical signal or data value corresponding to the detected state. According to an embodiment of the disclosure, the sensor module 1076 may include, for example, a gesture sensor, a gyro sensor, an atmospheric pressure sensor, a magnetic sensor, an acceleration sensor, a grip sensor, a proximity sensor, a color sensor, an infrared (IR) sensor, a biometric sensor, a temperature sensor, a humidity sensor, or an illuminance sensor.

The interface 1077 may support one or more specified protocols to be used for the electronic device 1001 to be coupled with the external electronic device (e.g., the external electronic device 1002) directly (e.g., wiredly) or wirelessly. According to an embodiment of the disclosure, the interface 1077 may include, for example, a high definition multimedia interface (HDMI), a universal serial bus (USB) interface, a secure digital (SD) card interface, or an audio interface.

A connecting terminal 1078 may include a connector via which the electronic device 1001 may be physically connected with the external electronic device (e.g., the external electronic device 1002). According to an embodiment of the disclosure, the connecting terminal 1078 may include, for example, a HDMI connector, a USB connector, an SD card connector, or an audio connector (e.g., a headphone connector).

The haptic module 1079 may convert an electrical signal into a mechanical stimulus (e.g., a vibration or a movement) or electrical stimulus which may be recognized by a user via his tactile sensation or kinesthetic sensation. According to an embodiment of the disclosure, the haptic module 1079 may include, for example, a motor, a piezoelectric element, or an electric stimulator.

The camera module 1080 may capture a still image or moving images. According to an embodiment of the disclosure, the camera module 1080 may include one or more lenses, image sensors, image signal processors, or flashes.

The power management module 1088 may manage power supplied to the electronic device 1001. According to one embodiment of the disclosure, the power management module 1088 may be implemented as at least part of, for example, a power management integrated circuit (PMIC).

The battery 1089 may supply power to at least one component of the electronic device 1001. According to an embodiment of the disclosure, the battery 1089 may include, for example, a primary cell which is not rechargeable, a secondary cell which is rechargeable, or a fuel cell.

The communication module 1090 may support establishing a direct (e.g., wired) communication channel or a wireless communication channel between the electronic device 1001 and the external electronic device (e.g., the external electronic device 1002, the external electronic device 1004, or the server 1008) and performing communication via the established communication channel. The communication module 1090 may include one or more communication processors that are operable independently from the processor 1020 (e.g., the application processor (AP)) and supports a direct (e.g., wired) communication or a wireless communication. According to an embodiment of the disclosure, the communication module 1090 may include a wireless communication module 1092 (e.g., a cellular communication module, a short-range wireless communication module, or a global navigation satellite system (GNSS) communication module) or a wired communication module 1094 (e.g., a local area network (LAN) communication module or a power line communication (PLC) module). A corresponding one of these communication modules may communicate with the external electronic device via the first network 1098 (e.g., a short-range communication network, such as Bluetooth™, wireless-fidelity (Wi-Fi) direct, or infrared data association (IrDA)) or the second network 1099 (e.g., a long-range communication network, such as a legacy cellular network, a 5G network, a next-generation communication network, the Internet, or a computer network (e.g., LAN or wide area network (WAN)). These various types of communication modules may be implemented as a single component (e.g., a single chip), or may be implemented as multi components (e.g., multi chips) separate from each other. The wireless communication module 1092 may identify and authenticate the electronic device 1001 in a communication network, such as the first network 1098 or the second network 1099, using subscriber information (e.g., international mobile subscriber identity (IMSI)) stored in the subscriber identification module 1096.

The wireless communication module 1092 may support a 5G network, after a $4^{th}$ generation (4G) network, and next-generation communication technology, e.g., new radio (NR) access technology. The NR access technology may support enhanced mobile broadband (eMBB), massive machine type communications (mMTC), or ultra-reliable and low-latency communications (URLLC). The wireless communication module 1092 may support a high-frequency band (e.g., the mmWave band) to achieve, e.g., a high data transmission rate. The wireless communication module 1092 may support various technologies for securing performance on a high-frequency band, such as, e.g., beamforming, massive multiple-input and multiple-output (massive MIMO), full dimensional MIMO (FD-MIMO), array antenna, analog beam-forming, or large scale antenna. The wireless communication module 1092 may support various requirements specified in the electronic device 1001, an external electronic device (e.g., the external electronic device 1004), or a network system (e.g., the second network 1099). According to an embodiment of the disclosure, the wireless communication module 1092 may support a peak data rate (e.g., 20 Gbps or more) for implementing eMBB, loss coverage (e.g., 1064 dB or less) for implementing mMTC, or U-plane latency (e.g., 0.5 ms or less for each of downlink (DL) and uplink (UL), or a round trip of 10 ms or less) for implementing URLLC.

The antenna module 1097 may transmit or receive a signal or power to or from the outside (e.g., the external electronic device) of the electronic device 1001. According to an embodiment of the disclosure, the antenna module 1097 may include an antenna including a radiating element including a conductive material or a conductive pattern formed in or on a substrate (e.g., a printed circuit board (PCB)). According to an embodiment of the disclosure, the antenna module 1097 may include a plurality of antennas (e.g., array antennas). In such a case, at least one antenna appropriate for a communication scheme used in the communication network, such as the first network 1098 or the second network 1099, may be selected, for example, by the communication module 1090 (e.g., the wireless communication module 1092) from the plurality of antennas. The signal or the power may then be transmitted or received between the communication module 1090 and the external electronic device via the selected at least one antenna. According to an embodiment of the disclosure, another component (e.g., a radio frequency integrated circuit (RFIC)) other than the radiating element may be additionally formed as part of the antenna module 1097.

According to various embodiments of the disclosure, the antenna module 1097 may form a mmWave antenna module. According to an embodiment of the disclosure, the mmWave antenna module may include a printed circuit board, a RFIC disposed on a first surface (e.g., the bottom surface) of the printed circuit board, or adjacent to the first surface and capable of supporting a designated high-frequency band (e.g., the mmWave band), and a plurality of antennas (e.g., array antennas) disposed on a second surface (e.g., the top or a side surface) of the printed circuit board, or adjacent to the second surface and capable of transmitting or receiving signals of the designated high-frequency band.

At least some of the above-described components may be coupled mutually and communicate signals (e.g., commands or data) therebetween via an inter-peripheral communication scheme (e.g., a bus, general purpose input and output (GPIO), serial peripheral interface (SPI), or mobile industry processor interface (MIPI)).

According to an embodiment of the disclosure, commands or data may be transmitted or received between the electronic device 1001 and the external electronic device 1004 via the server 1008 coupled with the second network 1099. Each of the external electronic devices 1002 or 1004 may be a device of a same type as, or a different type, from the electronic device 1001. According to an embodiment of the disclosure, all or some of operations to be executed at the electronic device 1001 may be executed at one or more of the external electronic devices 1002, 1004, or 1008. For example, if the electronic device 1001 should perform a function or a service automatically, or in response to a request from a user or another device, the electronic device 1001, instead of, or in addition to, executing the function or the service, may request the one or more external electronic devices to perform at least part of the function or the service. The one or more external electronic devices receiving the request may perform the at least part of the function or the service requested, or an additional function or an additional service related to the request, and transfer an outcome of the performing to the electronic device 1001. The electronic device 1001 may provide the outcome, with or without further processing of the outcome, as at least part of a reply to the request. To that end, a cloud computing, distributed computing, mobile edge computing (MEC), or client-server computing technology may be used, for example. The electronic device 1001 may provide ultra low-latency services using, e.g., distributed computing or mobile edge computing. In another embodiment of the disclosure, the external electronic device 1004 may include an internet-of-things (IoT) device. The server 1008 may be an intelligent server using machine learning and/or a neural network. According to an embodiment of the disclosure, the external electronic device 1004 or the server 1008 may be included in the second network 1099. The electronic device 1001 may be applied to intelligent services (e.g., smart home, smart city, smart car, or healthcare) based on 5G communication technology or IoT-related technology.

The electronic device according to various embodiments may be one of various types of electronic devices. The electronic devices may include, for example, a portable communication device (e.g., a smartphone), a computer device, a portable multimedia device, a portable medical device, a camera, a wearable device, or a home appliance. According to an embodiment of the disclosure, the electronic devices are not limited to those described above.

It should be appreciated that various embodiments of the disclosure and the terms used therein are not intended to limit the technological features set forth herein to particular embodiments and include various changes, equivalents, or replacements for a corresponding embodiment of the disclosure. With regard to the description of the drawings, similar reference numerals may be used to refer to similar or related elements. As used herein, each of such phrases as "A or B," "at least one of A and B," "at least one of A or B," "A, B, or C," "at least one of A, B, and C," and "at least one of A, B, or C," may include any one of, or all possible combinations of the items enumerated together in a corresponding one of the phrases. As used herein, such terms as "1st" and "2nd," or "first" and "second" may be used to simply distinguish a corresponding component from another, and does not limit the components in other aspect (e.g., importance or order). It is to be understood that if an element (e.g., a first element) is referred to, with or without the term "operatively" or "communicatively", as "coupled with," "coupled to," "connected with," or "connected to" another element (e.g., a second element), it means that the element may be coupled with the other element directly (e.g., wiredly), wirelessly, or via a third element.

As used in connection with various embodiments of the disclosure, the term "module" may include a unit implemented in hardware, software, or firmware, and may interchangeably be used with other terms, for example, "logic," "logic block," "part," or "circuitry". A module may be a single integral component, or a minimum unit or part thereof, adapted to perform one or more functions. For example, according to an embodiment of the disclosure, the module may be implemented in a form of an application-specific integrated circuit (ASIC).

Various embodiments as set forth herein may be implemented as software (e.g., the program 1040) including one or more instructions that are stored in a storage medium (e.g., an internal memory 1036 or an external memory 1038) that is readable by a machine (e.g., the electronic device 1001). For example, a processor (e.g., the processor 1020) of the machine (e.g., the electronic device 1001) may invoke at least one of the one or more instructions stored in the storage medium, and execute it, with or without using one or more other components under the control of the processor. This allows the machine to be operated to perform at least one function according to the at least one instruction invoked. The one or more instructions may include a code generated by a complier or a code executable by an interpreter. The machine-readable storage medium may be provided in the form of a non-transitory storage medium. Wherein, the term "non-transitory" simply means that the storage medium is a tangible device, and does not include a signal (e.g., an electromagnetic wave), but this term does not differentiate between where data is semi-permanently stored in the storage medium and where the data is temporarily stored in the storage medium.

According to an embodiment of the disclosure, a method according to various embodiments of the disclosure may be included and provided in a computer program product. The computer program product may be traded as a product between a seller and a buyer. The computer program product may be distributed in the form of a machine-readable storage medium (e.g., a compact disc read only memory (CD-ROM)), or be distributed (e.g., downloaded or uploaded) online via an application store (e.g., PlayStore™), or between two user devices (e.g., smart phones) directly. If distributed online, at least part of the computer program product may be temporarily generated or at least temporarily stored in the machine-readable storage medium, such as memory of the manufacturer's server, a server of the application store, or a relay server.

According to various embodiments of the disclosure, each component (e.g., a module or a program) of the above-described components may include a single entity or multiple entities, and some of the multiple entities may be separately disposed in different components. According to various embodiments of the disclosure, one or more of the above-described components may be omitted, or one or more other components may be added. Alternatively or additionally, a plurality of components (e.g., modules or programs) may be integrated into a single component. In such a case, according to various embodiments of the disclosure, the integrated component may still perform one or more functions of each of the plurality of components in the same or similar manner as they are performed by a corresponding one of the plurality of components before the integration. According to various embodiments of the disclosure, operations performed by the module, the program, or another component may be carried out sequentially, in parallel, repeatedly, or heuristically, or one or more of the operations may be executed in a different order or omitted, or one or more other operations may be added.

An electronic device (e.g., one of the electronic device 100 of FIGS. 1 and 2, the wearable device 101 of FIG. 1, and the mobile device 105 of FIG. 1) according to various embodiments may include a communication circuit (e.g., the communication circuit 130 of FIG. 2), a memory (e.g., the memory 120 of FIG. 2), and at least one processor (e.g., the processor 110 of FIG. 2) operatively connected to the communication circuit and the memory. The memory may store instructions which, when executed, cause the at least one processor to acquire real-time sleep data of a user with regard to a unit sleep session, detect an abnormal rapid eye movement (REM) sleep event based on the real-time sleep data and the user's previous sleep data with regard to a full sleep session, and provide a user interface based on designated action information in response to the abnormal REM sleep event.

According to various embodiments of the disclosure, the abnormal REM sleep event may be detected based on at least one of a time of entering a first REM sleep stage, a frequency of occurrence of a REM sleep stage, a duration of the REM sleep stage, and an interval between REM sleep stages.

According to various embodiments of the disclosure, the previous sleep data may correspond to data regarding the user's past sleep activity repeated a designated number of times or more, or the user's past sleep data for a recent predetermined period.

According to various embodiments of the disclosure, the instructions may be configured to cause the at least one processor to identify personalized boundary information for detecting the user's REM sleep stage from the previous sleep data, determine whether a pattern of the REM sleep stage is an abnormal pattern based on the real-time sleep data and the personalized boundary information, and detect the abnormal REM sleep event based on that the pattern of the REM sleep stage is the abnormal pattern.

According to various embodiments of the disclosure, the personalized boundary information is feature information of a cardiac activity signal measured during the full sleep session, and the feature information may include one or more of an LF value (power in low frequency range), an HF value (power in high frequency range), and an LF/HF value (ratio of LF to HF).

According to various embodiments of the disclosure, the action information may include information regarding at least one action of an alarm output, a vibration output, a lighting control, and audio reproduction.

According to various embodiments of the disclosure, the action information may include information regarding an action for inducing the user to wake up or an action for inducing the user to fall into deep sleep.

According to various embodiments of the disclosure, the instructions may be configured to cause the at least one processor to provide a user interface related to the action information through an output module (e.g., the output module 150 of FIG. 2) in the electronic device, or perform short-range wireless communication with at least one external electronic device (e.g., the IoT device 200, the wearable device 101, and the mobile device 105 of FIG. 1) through the communication circuit to provide a user interface related to the action information through the at least one external electronic device.

According to various embodiments of the disclosure, the instructions may be configured to cause the at least one processor to obtain real-time sleep data with regard to a full sleep session by accumulating real-time sleep data with regard to multiple unit sleep sessions, and transmit, to a server through the communication circuit, at least one of the real-time sleep data with regard to the full sleep session, information regarding the abnormal REM sleep event, and action execution information related to the abnormal REM sleep event.

According to various embodiments of the disclosure, the real-time sleep data may include data regarding one or more of a biometric signal measured through a first sensor in the electronic device, a biometric signal received from an external electronic device through the communication circuit, a motion signal measured through a second sensor in the electronic device, or a motion signal received from the external electronic device through the communication circuit.

A method for operating an electronic device according to various embodiments may include acquiring real-time sleep data of a user with regard to a unit sleep session, detecting an abnormal rapid eye movement (REM) sleep event based on the real-time sleep data and the user's previous sleep data with regard to a full sleep session, and providing a user interface based on designated action information in response to the abnormal REM sleep event.

According to various embodiments of the disclosure, the abnormal REM sleep event may be detected based on at least one of a time of entering a first REM sleep stage, a frequency of occurrence of a REM sleep stage, a duration of the REM sleep stage, and an interval between REM sleep stages.

According to various embodiments of the disclosure, the previous sleep data corresponds to data regarding the user's past sleep activity repeated a designated number of times or more, or the user's past sleep data for a recent predetermined period.

According to various embodiments of the disclosure, the detecting of the abnormal REM sleep event may include identifying personalized boundary information for detecting the user's REM sleep stage from the previous sleep data, determining whether a pattern of the REM sleep stage is an abnormal pattern based on the real-time sleep data and the personalized boundary information, and detecting the abnormal REM sleep event based on that the pattern of the REM sleep stage is the abnormal pattern.

According to various embodiments of the disclosure, the personalized boundary information is feature information of a cardiac activity signal measured during the full sleep session, and the feature information may include one or more of an LF value (power in low frequency range), an HF value (power in high frequency range), and an LF/HF value (ratio of LF to HF).

According to various embodiments of the disclosure, the action information may include information regarding at least one action of alarm output, vibration output, lighting control, and audio reproduction.

According to various embodiments of the disclosure, the action information may include information regarding an action for inducing the user to wake up or an action for inducing the user to fall into deep sleep.

According to various embodiments of the disclosure, the providing of the user interface may include at least one of providing a user interface related to the action information through an output module in the electronic device, and performing short-range wireless communication with at least one external electronic device through the communication circuit in the electronic device so as to provide the user interface related to the action information through the at least one external electronic device.

The method for operating the electronic device according to various embodiments may further include obtaining real-time sleep data with regard to a full sleep session by accumulating real-time sleep data with regard to multiple unit sleep sessions, and transmitting one or more of the real-time sleep data with regard to the full sleep session, information regarding the abnormal REM sleep event, and action execution information to a server.

According to various embodiments of the disclosure, the real-time sleep data may include data regarding one or more of a biometric signal measured through a first sensor in the electronic device, a biometric signal received from an external electronic device, a motion signal measured through a second sensor in the electronic device, or a motion signal received from the external electronic device.

The method for operating the electronic device according to various embodiments may further include operating an application in the external electronic device or the electronic device, and configuring through an app execution screen one or more actions to be performed when the abnormal REM sleep event occurs.

According to various embodiments of the disclosure, the application may include at least one of a health care application or a sleep care application.

While the disclosure has been shown and described with reference to various embodiments thereof, it will be understood by those skilled in the art that various changes in form and details may be made therein without departing from the spirit and scope of the disclosure as defined by the appended claims and their equivalents.

What is claimed is:

1. An electronic device comprising:

communication circuit circuitry;

memory; and at least one processor, wherein the memory stores instructions which, when executed by the at least one processor, cause the electronic device to:

store reference information regarding rapid eye movement (REM) sleep stages based on previous sleep data of a user for a long-term sleep session, wherein the long-term sleep session includes multiple short-term sleep sessions, acquire real-time sleep data of the user for at least one short-term sleep session, identify REM sleep information regarding at least one REM sleep stage based on the real-time sleep data, wherein the REM sleep information includes information about at least one of a time of entry into a first REM sleep stage, a frequency of REM sleep stages, a number of the REM sleep stages, a duration of a REM sleep stage, or an interval between the REM sleep stages, detect an occurrence of a designated event based on a comparison of the REM sleep information and the reference information, and provide a user interface based on designated action information in response to detecting the occurrence of the designated event.

2. The electronic device of claim 1, wherein the instructions are configured to cause the electronic device to at least one of:

provide, as at least part of the user interface, a visual type user interface at least in part by at least one of output of information via a display or control of a lamp, provide, as at least part of the user interface, a tactile type user interface at least in part by output of vibration via a haptic module, or provide, as at least part of the user interface, an audible type user interface at least in part by output of reproduced audio or alarm via speaker.

3. The electronic device of claim 1, wherein the previous sleep data corresponds to data regarding past sleep activity of the user repeated a designated number of times, or past sleep data of the user for a predetermined period.

4. The electronic device of claim 1, wherein the instructions are further configured to cause the electronic device to:

identify personalized boundary information as the reference information for detecting a REM sleep stage of the user from the previous sleep data, determine whether a pattern of the REM sleep stage corresponds to a pattern of the designated event based on a comparison of the REM sleep information from the real-time sleep data and the personalized boundary information from the previous sleep data, and detect the occurrence of the designated event based on the pattern of the REM sleep stage being determined to correspond to the pattern of the designated event.

5. The electronic device of claim 4, wherein the personalized boundary information is feature information of a cardiac activity signal measured during the long-term sleep session, and wherein the feature information includes at least one of a low frequency (LF) value that denotes power in a LF range, a high frequency (HF) value that denotes power in a HF range, or an LF/HF value that denotes a ratio of LF to Hf.

6. The electronic device of claim 1, wherein the action information includes information regarding at least one action respectively of at least one of alarm output, vibration output, lighting control, or audio reproduction.

7. The electronic device of claim 1, wherein the action information includes information regarding an action for inducing the user to wake up.

8. The electronic device of claim 1, wherein the instructions are further configured to cause the electronic device to at least one of:

provide the user interface based on the designated action information through at least one of a display, a haptic module, or a speaker of the electronic device, or perform short-range wireless communication with at least one external electronic device through the communication circuitry to provide the user interface based on the designated action information through the at least one external electronic device.

9. The electronic device of claim 1, wherein the instructions are further configured to cause the electronic device to:

obtain real-time sleep data for the long-term sleep session by accumulating real-time sleep data for the multiple short-term sleep sessions, and transmit, to a server through the communication circuitry, at least one of the real-time sleep data for the long-term sleep session, information regarding the designated event, or action execution information related to the designated event.

10. The electronic device of claim 1, wherein the real-time sleep data comprises data regarding at least one of:

a biometric signal measured through a first sensor in the electronic device, a biometric signal received from an external electronic device through the communication circuitry, a motion signal measured through a second sensor in the electronic device, or a motion signal received from the external electronic device through the communication circuitry.

11. A method performed by an electronic device, the method comprising:

storing reference information regarding rapid eye movement (REM) sleep stages based on previous sleep data of a user for a long-term sleep session, wherein the long-term sleep session includes multiple short-term sleep sessions;

acquiring real-time sleep data of the user for at least one short-term sleep session;

identifying REM sleep information regarding at least one REM sleep stage based on the real-time sleep data, wherein the REM sleep information includes information about at least one of a time of entry into a first REM sleep stage, a frequency of REM sleep stages, a number of the REM sleep stages, a duration of a REM sleep stage, or an interval between the REM sleep stages;

detecting an occurrence of a designated event based on a comparison of the REM sleep information and the reference information; and providing a user interface based on designated action information in response to detecting the occurrence of the designated event.

12. The method of claim 11, wherein the providing of the user interface comprises at least one of:

providing, as at least part of the user interface, a visual type user interface at least in part by at least one of outputting information via a display or controlling of a lamp;

providing, as at least part of the user interface, a tactile type user interface at least in part by outputting vibration via a haptic module; or providing, as at least part of the user interface, an audible type user interface at least in part by outputting reproduced audio or alarm via speaker.

13. The method of claim 11, wherein the previous sleep data corresponds to data regarding past sleep activity of the user repeated a designated number of times, or past sleep data of the user for a predetermined period.

14. The method of claim 11, wherein the detecting of the occurrence of the designated event comprises:

identifying personalized boundary information as the reference information for detecting REM sleep stage of the user from the previous sleep data;

determining whether a pattern of the REM sleep stage corresponds to a pattern of the designated event based on a comparison of the REM sleep information from the real-time sleep data and the personalized boundary information from the previous sleep data; and detecting the occurrence of the designated event based on the pattern of the REM sleep stage being determined to correspond to the pattern of the designated event.

15. The method of claim 14, wherein the personalized boundary information is feature information of a cardiac activity signal measured during the long-term sleep session, and wherein the feature information includes at least one of a low frequency (LF) value that denotes power in a LF range, a high frequency (HF) value that denotes power in a HF range, or an LF/HF value that denotes a ratio of LF to Hf.

16. The method of claim 11, wherein the action information includes information regarding at least one action respectively of at least one of alarm output, vibration output, lighting control, or audio reproduction.

17. The method of claim 11, wherein the action information includes information regarding an action for inducing the user to wake up.

18. The method of claim 11, wherein the providing of the user interface comprises at least one of:

providing the user interface based on the designated action information through at least one of a display, a haptic module, or a speaker of the electronic device; or performing short-range wireless communication with at least one external electronic device through communication circuitry in the electronic device so as to provide the user interface based on the designated action information through the at least one external electronic device.

19. The method of claim 11, further comprising:

obtaining real-time sleep data for the long-term sleep session by accumulating real-time sleep data for the multiple unit-short-term sleep sessions; and transmitting, to a server, at least one of the real-time sleep data for the long-term sleep session, information regarding the designated event, or action execution information related to the designated event.

20. The method of claim 11, wherein the real-time sleep data comprises data regarding at least one of:

a biometric signal measured through a first sensor in the electronic device, a biometric signal received from an external electronic device, a motion signal measured through a second sensor in the electronic device, or a motion signal received from the external electronic device.

* * * * *